United States Patent
Connor et al.

(10) Patent No.: US 9,907,684 B2
(45) Date of Patent: Mar. 6, 2018

(54) METHOD OF RADIALLY-ASYMMETRIC STENT EXPANSION

(71) Applicants: Robert A. Connor, Forest Lake, MN (US); Tariq M. Janjua, Inver Grove Heights, MN (US)

(72) Inventors: Robert A. Connor, Forest Lake, MN (US); Tariq M. Janjua, Inver Grove Heights, MN (US)

(73) Assignee: Aneuclose LLC, St. Paul, MN (US)

( * ) Notice: Subject to any disclaimer, the term of this patent is extended or adjusted under 35 U.S.C. 154(b) by 702 days.

(21) Appl. No.: 13/889,451

(22) Filed: May 8, 2013

(65) Prior Publication Data

US 2014/0336741 A1    Nov. 13, 2014

(51) Int. Cl.
*A61F 2/958* (2013.01)
*A61F 2/915* (2013.01)
*A61F 2/82* (2013.01)

(52) U.S. Cl.
CPC .............. *A61F 2/958* (2013.01); *A61F 2/915* (2013.01); *A61F 2002/823* (2013.01); *A61F 2002/91575* (2013.01); *A61F 2250/0023* (2013.01)

(58) Field of Classification Search
CPC .... A61F 2/958; A61F 2/915; A61F 2002/823; A61F 2250/0023; A61F 2002/91575; A61F 2/82; A61F 2/86
USPC ...................................................... 623/1.11
See application file for complete search history.

(56) References Cited

U.S. PATENT DOCUMENTS

| | | |
|---|---|---|
| 5,226,889 A | 7/1993 | Sheiban |
| 5,258,042 A | 11/1993 | Mehta |
| 5,304,132 A | 4/1994 | Jang |
| 5,308,323 A | 5/1994 | Sogawa et al. |
| 5,411,549 A | 5/1995 | Peters |
| 5,441,515 A | 8/1995 | Khosravi et al. |
| 5,443,495 A | 8/1995 | Buscemi et al. |
| 5,464,449 A | 11/1995 | Ryan et al. |
| 5,536,252 A | 7/1996 | Imran et al. |
| 5,545,209 A | 8/1996 | Roberts et al. |
| 5,603,722 A | 2/1997 | Phan et al. |
| 5,693,088 A | 12/1997 | Lazarus |
| 5,704,913 A | 1/1998 | Abele et al. |
| 5,723,004 A | 3/1998 | Dereume et al. |
| 5,749,894 A | 5/1998 | Engelson |
| 5,755,781 A | 5/1998 | Jayaraman |
| 5,769,884 A | 6/1998 | Solovay |
| 5,833,657 A | 11/1998 | Reinhardt et al. |
| 5,836,966 A | 11/1998 | St. Germain |

(Continued)

*Primary Examiner* — Christopher L Templeton
*Assistant Examiner* — George J Ulsh

(57) ABSTRACT

This invention gives physicians in situ control to create differences in wall porosity between different areas of a stent wall. This enables a physician to customize the stent within a blood vessel to selectively block blood flow to an aneurysm with a low-porosity area of the stent wall, but allow blood flow to nearby branching vessels through one or more high-porosity areas of the stent wall. The method comprises inserting a stent into a blood vessel and, in situ, expanding the stent in a non-uniform manner, thereby causing one or more areas of the stent wall to have a lower post-expansion porosity than the rest of the stent wall. With this invention, physicians can selectively block blood flow into an aneurysm while maintaining blood flow into nearby branching vessels, even in tortuous and complex vessel configurations.

1 Claim, 12 Drawing Sheets

(56) References Cited

U.S. PATENT DOCUMENTS

| | | |
|---|---|---|
| 5,843,158 A | 12/1998 | Lenker et al. |
| 5,868,780 A | 2/1999 | Lashinski et al. |
| 5,873,907 A | 2/1999 | Frantzen |
| 5,908,448 A | 6/1999 | Roberts et al. |
| 5,911,754 A | 6/1999 | Kanesaka et al. |
| 5,922,019 A | 7/1999 | Hankh et al. |
| 5,938,697 A | 8/1999 | Killion et al. |
| 5,948,018 A | 9/1999 | Dereume et al. |
| 5,951,599 A | 9/1999 | McCrory |
| 5,957,975 A | 9/1999 | Lafont et al. |
| 5,964,744 A | 10/1999 | Balbierz et al. |
| 5,980,514 A | 11/1999 | Kupiecki et al. |
| 6,004,261 A | 12/1999 | Sinofsky et al. |
| 6,007,573 A | 12/1999 | Wallace et al. |
| 6,027,526 A | 2/2000 | Limon et al. |
| 6,030,414 A | 2/2000 | Taheri |
| 6,059,822 A | 5/2000 | Kanesaka et al. |
| 6,063,111 A | 5/2000 | Hieshima et al. |
| 6,071,298 A | 6/2000 | Lashinski et al. |
| 6,086,610 A | 7/2000 | Duerig et al. |
| 6,093,199 A | 7/2000 | Brown et al. |
| 6,096,034 A | 8/2000 | Kupiecki et al. |
| 6,099,559 A | 8/2000 | Nolting |
| 6,123,712 A | 9/2000 | Di Caprio et al. |
| 6,129,754 A | 10/2000 | Kanesaka et al. |
| 6,136,011 A | 10/2000 | Stambaugh |
| 6,139,564 A | 10/2000 | Teoh |
| 6,149,681 A | 11/2000 | Houser et al. |
| 6,159,238 A | 12/2000 | Killion et al. |
| 6,165,212 A | 12/2000 | Dereume et al. |
| 6,168,615 B1 | 1/2001 | Ken et al. |
| 6,168,622 B1 | 1/2001 | Mazzocchi |
| 6,190,406 B1 | 2/2001 | Duerig et al. |
| 6,210,429 B1 | 4/2001 | Vardi et al. |
| 6,231,597 B1 | 5/2001 | Deem et al. |
| 6,258,115 B1 | 7/2001 | Dubrul |
| 6,258,117 B1 | 7/2001 | Camrud et al. |
| 6,270,523 B1 | 8/2001 | Herweck et al. |
| 6,273,910 B1 | 8/2001 | Limon |
| 6,273,911 B1 | 8/2001 | Cox et al. |
| 6,296,660 B1 | 10/2001 | Roberts et al. |
| 6,309,367 B1 | 10/2001 | Boock |
| 6,309,413 B1 | 10/2001 | Dereume et al. |
| 6,312,421 B1 | 11/2001 | Boock |
| 6,312,463 B1 | 11/2001 | Rourke et al. |
| 6,315,791 B1 | 11/2001 | Gingras et al. |
| 6,331,191 B1 | 12/2001 | Chobotov |
| 6,340,366 B2 | 1/2002 | Wijay |
| 6,342,068 B1 | 1/2002 | Thompson |
| 6,344,041 B1 | 2/2002 | Kupiecki et al. |
| 6,395,018 B1 | 5/2002 | Castaneda |
| 6,398,803 B1 | 6/2002 | Layne et al. |
| 6,409,749 B1 | 6/2002 | Maynard |
| 6,416,543 B1 | 7/2002 | Hilaire et al. |
| 6,419,685 B2 | 7/2002 | Di Caprio et al. |
| 6,432,128 B1 | 8/2002 | Wallace et al. |
| 6,468,302 B2 | 10/2002 | Cox et al. |
| 6,471,672 B1 | 10/2002 | Brown et al. |
| 6,475,233 B2 | 11/2002 | Trozera |
| 6,475,236 B1 | 11/2002 | Roubin et al. |
| 6,485,509 B2 | 11/2002 | Killion et al. |
| 6,485,510 B1 | 11/2002 | Camrud et al. |
| 6,497,722 B1 | 12/2002 | Von Oepen et al. |
| 6,506,201 B2 | 1/2003 | Di Caprio et al. |
| 6,511,505 B2 | 1/2003 | Cox et al. |
| 6,520,985 B1 | 2/2003 | Burpee et al. |
| 6,520,987 B1 | 2/2003 | Plante |
| 6,558,414 B2 | 5/2003 | Layne |
| 6,569,193 B1 | 5/2003 | Cox et al. |
| 6,579,305 B1 | 6/2003 | Lashinski |
| 6,579,308 B1 | 6/2003 | Jansen et al. |
| 6,579,314 B1 | 6/2003 | Lombardi et al. |
| 6,585,753 B2 | 7/2003 | Eder et al. |
| 6,585,758 B1 | 7/2003 | Chouinard et al. |
| 6,599,316 B2 | 7/2003 | Vardi et al. |
| 6,602,284 B2 | 8/2003 | Cox et al. |
| 6,605,056 B2 | 8/2003 | Eidenschink et al. |
| 6,605,111 B2 | 8/2003 | Bose et al. |
| 6,607,539 B1 | 8/2003 | Hayashi et al. |
| 6,610,087 B1 | 8/2003 | Zarbatany et al. |
| 6,645,237 B2 | 11/2003 | Klumb et al. |
| 6,652,576 B1 | 11/2003 | Stalker |
| 6,660,032 B2 | 12/2003 | Klumb et al. |
| 6,663,607 B2 | 12/2003 | Slaikeu et al. |
| 6,669,719 B2 | 12/2003 | Wallace et al. |
| 6,669,723 B2 | 12/2003 | Killion et al. |
| 6,673,103 B1 | 1/2004 | Golds et al. |
| 6,673,385 B1 | 1/2004 | Ding et al. |
| 6,676,692 B2 | 1/2004 | Rabkin et al. |
| 6,676,701 B2 | 1/2004 | Rourke et al. |
| 6,716,238 B2 | 4/2004 | Elliott |
| 6,719,783 B2 | 4/2004 | Lentz et al. |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,796,997 B1 | 9/2004 | Penn et al. |
| 6,805,706 B2 | 10/2004 | Solovay et al. |
| 6,811,560 B2 | 11/2004 | Jones et al. |
| 6,833,003 B2 | 12/2004 | Jones et al. |
| 6,835,203 B1 | 12/2004 | Vardi et al. |
| 6,837,901 B2 | 1/2005 | Rabkin et al. |
| 6,872,223 B2 | 3/2005 | Roberts et al. |
| 6,913,618 B2 | 7/2005 | Denardo et al. |
| 6,962,602 B2 | 11/2005 | Vardi et al. |
| 6,969,401 B1 | 11/2005 | Marotta et al. |
| 6,994,721 B2 | 2/2006 | Israel |
| 7,001,422 B2 | 2/2006 | Escamilla et al. |
| 7,029,492 B1 | 4/2006 | Mitsudou et al. |
| 7,033,385 B2 | 4/2006 | Eder et al. |
| 7,037,327 B2 | 5/2006 | Salmon et al. |
| 7,041,129 B2 | 5/2006 | Rourke et al. |
| 7,052,510 B1 | 5/2006 | Richter |
| 7,052,513 B2 | 5/2006 | Thompson |
| 7,060,091 B2 | 6/2006 | Killion et al. |
| 7,063,719 B2 | 6/2006 | Jansen et al. |
| 7,081,129 B2 | 7/2006 | Chobotov |
| 7,083,640 B2 | 8/2006 | Lombardi et al. |
| 7,112,216 B2 | 9/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,659 B2 | 12/2006 | Jones |
| 7,147,660 B2 | 12/2006 | Chobotov et al. |
| 7,147,661 B2 | 12/2006 | Chobotov et al. |
| 7,156,871 B2 | 1/2007 | Jones et al. |
| 7,169,172 B2 | 1/2007 | Levine et al. |
| 7,186,263 B2 | 3/2007 | Golds et al. |
| 7,195,648 B2 | 3/2007 | Jones et al. |
| 7,211,109 B2 | 5/2007 | Thompson |
| 7,226,475 B2 | 6/2007 | Lenz et al. |
| 7,231,260 B2 | 6/2007 | Wallace et al. |
| 7,232,461 B2 | 6/2007 | Ramer |
| 7,235,098 B2 | 6/2007 | Palmaz |
| 7,241,308 B2 | 7/2007 | Andreas et al. |
| 7,288,112 B2 | 10/2007 | Denardo et al. |
| 7,294,146 B2 | 11/2007 | Chew et al. |
| 7,306,624 B2 | 12/2007 | Yodfat et al. |
| 7,309,351 B2 | 12/2007 | Escamilla et al. |
| 7,309,352 B2 | 12/2007 | Eder et al. |
| 7,323,005 B2 | 1/2008 | Wallace et al. |
| 7,326,236 B2 | 2/2008 | Andreas et al. |
| 7,384,426 B2 | 6/2008 | Wallace et al. |
| 7,402,169 B2 | 7/2008 | Killion et al. |
| 7,413,573 B2 | 8/2008 | Hartley et al. |
| 7,491,226 B2 | 2/2009 | Palmaz et al. |
| 7,491,229 B2 | 2/2009 | Eder et al. |
| 7,527,644 B2 | 5/2009 | Mangiardi et al. |
| 7,537,609 B2 | 5/2009 | Davidson et al. |
| 7,547,321 B2 | 6/2009 | Silvestri et al. |
| 7,563,270 B2 | 7/2009 | Gumm |
| 7,572,288 B2 | 8/2009 | Cox |
| 7,572,290 B2 | 8/2009 | Yodfat et al. |
| 7,608,088 B2 | 10/2009 | Jones et al. |

(56) References Cited

U.S. PATENT DOCUMENTS

| | | |
|---|---|---|
| 7,611,530 B2 | 11/2009 | Pomeranz et al. |
| 7,615,071 B2 | 11/2009 | Chobotov |
| 7,621,928 B2 | 11/2009 | Thramann et al. |
| 7,637,942 B2 | 12/2009 | Mangiardi et al. |
| 7,641,680 B2 | 1/2010 | Palmaz et al. |
| 7,645,298 B2 | 1/2010 | Hartley et al. |
| 7,651,525 B2 | 1/2010 | Dolan |
| 7,666,220 B2 | 2/2010 | Evans et al. |
| 7,695,488 B2 | 4/2010 | Berenstein et al. |
| 7,695,509 B2 | 4/2010 | Rourke et al. |
| 7,722,657 B2 | 5/2010 | Hartley |
| 7,763,011 B2 | 7/2010 | Ortiz et al. |
| 7,766,955 B2 | 8/2010 | Vardi et al. |
| 7,776,079 B2 | 8/2010 | Gumm |
| 7,780,719 B2 | 8/2010 | Killion et al. |
| 7,823,263 B2 | 11/2010 | Wu |
| 7,850,725 B2 | 12/2010 | Vardi et al. |
| 7,857,843 B2 | 12/2010 | Henderson |
| 7,862,602 B2 | 1/2011 | Licata et al. |
| 7,862,608 B2 | 1/2011 | Hogendijk et al. |
| 7,892,273 B2 | 2/2011 | George et al. |
| 7,892,279 B2 | 2/2011 | Davidson et al. |
| 7,901,445 B2 | 3/2011 | Wallace et al. |
| 7,905,913 B2 | 3/2011 | Chew et al. |
| 7,914,574 B2 | 3/2011 | Schmid et al. |
| 7,914,639 B2 | 3/2011 | Layne et al. |
| 7,918,881 B2 | 4/2011 | Andreas et al. |
| 7,922,755 B2 | 4/2011 | Acosta et al. |
| 7,935,142 B2 | 5/2011 | Gregorich |
| 7,942,847 B2 | 5/2011 | Stupecky et al. |
| 7,942,925 B2 | 5/2011 | Yodfat et al. |
| 7,947,071 B2 | 5/2011 | Schmid et al. |
| 7,959,662 B2 | 6/2011 | Erbel et al. |
| 7,959,671 B2 | 6/2011 | Mangiardi et al. |
| 7,963,987 B2 | 6/2011 | Melsheimer et al. |
| 7,988,719 B2 | 8/2011 | Alt et al. |
| 7,988,721 B2 | 8/2011 | Morris et al. |
| 7,993,385 B2 | 8/2011 | Levine et al. |
| 7,998,189 B2 | 8/2011 | Kolbel et al. |
| 8,007,527 B2 | 8/2011 | Thompson |
| 8,007,529 B2 | 8/2011 | Yan |
| RE42,758 E | 9/2011 | Ken et al. |
| 8,012,192 B2 | 9/2011 | Eidenschink et al. |
| 8,012,196 B2 | 9/2011 | Smith et al. |
| 8,012,197 B2 | 9/2011 | Bashiri et al. |
| 8,016,853 B2 | 9/2011 | Griffen et al. |
| 8,016,870 B2 | 9/2011 | Chew et al. |
| 8,016,871 B2 | 9/2011 | Chew et al. |
| 8,016,876 B2 | 9/2011 | Gregorich et al. |
| 8,016,878 B2 | 9/2011 | Meyer et al. |
| 8,021,416 B2 | 9/2011 | Abrams |
| 8,038,706 B2 | 10/2011 | Eidenschink et al. |
| 2001/0016766 A1 | 8/2001 | Vardi et al. |
| 2001/0037137 A1 | 11/2001 | Vardi et al. |
| 2002/0045914 A1 | 4/2002 | Roberts et al. |
| 2002/0116047 A1 | 8/2002 | Vardi et al. |
| 2002/0156516 A1 | 10/2002 | Vardi et al. |
| 2003/0014007 A1 | 1/2003 | Eidenschink et al. |
| 2003/0065375 A1 | 4/2003 | Eskuri |
| 2003/0074049 A1 | 4/2003 | Hoganson et al. |
| 2003/0074056 A1 | 4/2003 | Killion et al. |
| 2003/0100945 A1 | 5/2003 | Yodfat et al. |
| 2003/0109917 A1 | 6/2003 | Rudin et al. |
| 2003/0139802 A1 | 7/2003 | Wulfman et al. |
| 2004/0015227 A1 | 1/2004 | Vardi et al. |
| 2004/0044391 A1 | 3/2004 | Porter |
| 2004/0073289 A1 | 4/2004 | Hartley |
| 2004/0111142 A1 | 6/2004 | Rourke et al. |
| 2004/0186551 A1 | 9/2004 | Kao et al. |
| 2004/0215312 A1 | 10/2004 | Andreas |
| 2004/0243216 A1 | 12/2004 | Gregorich |
| 2004/0249435 A1 | 12/2004 | Andreas et al. |
| 2004/0249439 A1 | 12/2004 | Richter et al. |
| 2004/0260384 A1 | 12/2004 | Allen |
| 2005/0055077 A1 | 3/2005 | Marco et al. |
| 2005/0107863 A1 | 5/2005 | Brown |
| 2005/0119684 A1 | 6/2005 | Guterman et al. |
| 2005/0131518 A1 | 6/2005 | Hartley et al. |
| 2005/0149159 A1 | 7/2005 | Andreas et al. |
| 2005/0149166 A1 | 7/2005 | Schaeffer et al. |
| 2005/0171597 A1 | 8/2005 | Boatman et al. |
| 2005/0171598 A1 | 8/2005 | Schaeffer |
| 2005/0177186 A1 | 8/2005 | Cully et al. |
| 2005/0192620 A1 | 9/2005 | Cully et al. |
| 2005/0209674 A1 | 9/2005 | Kutscher et al. |
| 2005/0222668 A1 | 10/2005 | Schaeffer et al. |
| 2005/0267570 A1 | 12/2005 | Shadduck |
| 2005/0283220 A1 | 12/2005 | Gobran et al. |
| 2006/0058864 A1 | 3/2006 | Schaeffer et al. |
| 2006/0085061 A1 | 4/2006 | Vardi et al. |
| 2006/0095111 A1 | 5/2006 | Jones et al. |
| 2006/0206196 A1 | 9/2006 | Porter |
| 2006/0229714 A1 | 10/2006 | Lombardi et al. |
| 2006/0241740 A1 | 10/2006 | Vardi et al. |
| 2007/0021816 A1 | 1/2007 | Rudin |
| 2007/0060994 A1 | 3/2007 | Gobran et al. |
| 2007/0067015 A1 | 3/2007 | Jones et al. |
| 2007/0088368 A1 | 4/2007 | Acosta et al. |
| 2007/0100301 A1 | 5/2007 | Gumm |
| 2007/0150045 A1 | 6/2007 | Ferrera |
| 2007/0162106 A1* | 7/2007 | Evans ............... A61B 17/12118 623/1.23 |
| 2007/0179592 A1 | 8/2007 | Schaeffer |
| 2007/0207186 A1 | 9/2007 | Scanlon et al. |
| 2007/0219610 A1 | 9/2007 | Israel |
| 2007/0219619 A1 | 9/2007 | Dieck et al. |
| 2007/0225794 A1 | 9/2007 | Thramann et al. |
| 2007/0239261 A1 | 10/2007 | Bose et al. |
| 2007/0276469 A1 | 11/2007 | Tenne |
| 2007/0276470 A1 | 11/2007 | Tenne |
| 2007/0299498 A1 | 12/2007 | Perez et al. |
| 2008/0004653 A1 | 1/2008 | Sherman et al. |
| 2008/0039933 A1 | 2/2008 | Yodfat et al. |
| 2008/0097374 A1 | 4/2008 | Korleski et al. |
| 2008/0097495 A1 | 4/2008 | Feller et al. |
| 2008/0195137 A1 | 8/2008 | Alleyne et al. |
| 2008/0215018 A1 | 9/2008 | Duffy et al. |
| 2008/0312732 A1 | 12/2008 | Hartley et al. |
| 2009/0069880 A1 | 3/2009 | Vonderwalde et al. |
| 2009/0082846 A1 | 3/2009 | Chobotov |
| 2009/0125053 A1 | 5/2009 | Ferrera et al. |
| 2009/0132028 A1 | 5/2009 | Vardi et al. |
| 2009/0171437 A1 | 7/2009 | Brocker et al. |
| 2009/0275974 A1 | 11/2009 | Marchand et al. |
| 2009/0306763 A1 | 12/2009 | Roeder et al. |
| 2009/0318949 A1 | 12/2009 | Ganpath et al. |
| 2010/0042200 A1 | 2/2010 | Richter et al. |
| 2010/0063531 A1 | 3/2010 | Rudakov et al. |
| 2010/0069948 A1 | 3/2010 | Veznedaroglu et al. |
| 2010/0094247 A1 | 4/2010 | Kaluski |
| 2010/0106240 A1 | 4/2010 | Duggal et al. |
| 2010/0114302 A1 | 5/2010 | Tzafriri et al. |
| 2010/0131002 A1 | 5/2010 | Connor et al. |
| 2010/0161026 A1 | 6/2010 | Brocker et al. |
| 2010/0222804 A1 | 9/2010 | Murphy et al. |
| 2010/0228338 A1 | 9/2010 | Thompson |
| 2010/0305681 A1 | 12/2010 | Gumm |
| 2010/0312326 A1 | 12/2010 | Chuter et al. |
| 2010/0318173 A1 | 12/2010 | Kolandaivelu et al. |
| 2011/0022149 A1 | 1/2011 | Cox et al. |
| 2011/0046658 A1 | 2/2011 | Connor et al. |
| 2011/0082533 A1 | 4/2011 | Vardi et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0152996 A1 | 6/2011 | Acosta et al. |
| 2011/0160833 A1 | 6/2011 | Gonzalez et al. |
| 2011/0184452 A1 | 7/2011 | Huynh et al. |
| 2011/0184453 A1 | 7/2011 | Levy et al. |
| 2011/0190867 A1 | 8/2011 | Vonderwalde et al. |
| 2011/0224774 A1 | 9/2011 | Silveira et al. |
| 2011/0230951 A1 | 9/2011 | Cully et al. |

(56) References Cited

U.S. PATENT DOCUMENTS

| | | |
|---|---|---|
| 2011/0238105 A1 | 9/2011 | Gelbart et al. |
| 2013/0123901 A1* | 5/2013 | Connor .................... A61F 2/86 623/1.15 |
| 2014/0121746 A1* | 5/2014 | Kusleika ................... A61F 2/90 623/1.11 |

* cited by examiner

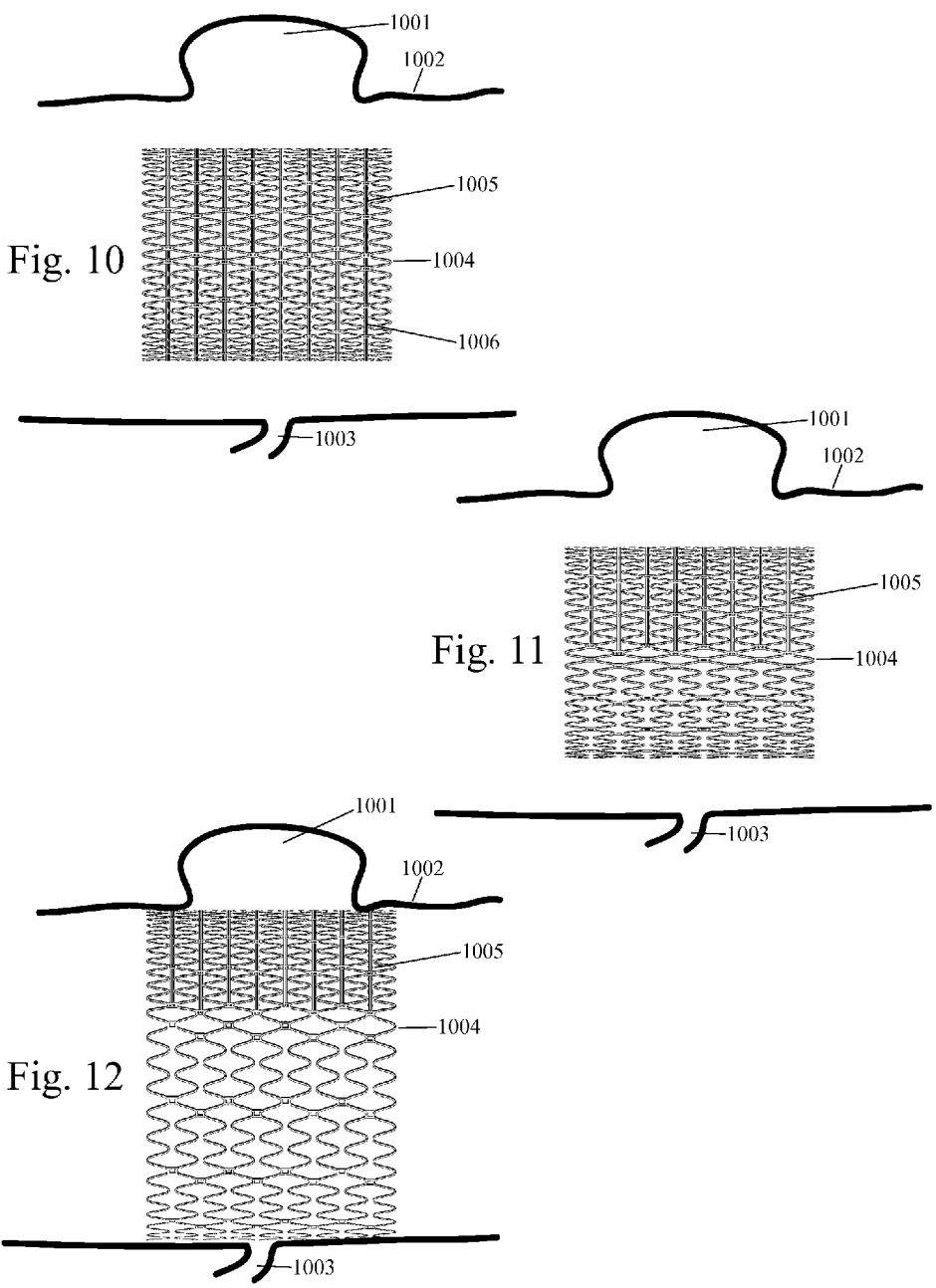

METHOD OF RADIALLY-ASYMMETRIC STENT EXPANSION

CROSS-REFERENCE TO RELATED APPLICATIONS

This is a division of U.S. patent application Ser. No. 13/373,424 which was filed on Nov. 14, 2011 entitled "Stent with In Situ Determination of Wall Areas with Differences in Porosity." U.S. patent application Ser. No. 13/373,424 was subject to restriction under 35 U.S.C. 121. The claims herein are for a non-elected species which was determined by the USPTO to be patentably distinct from the elected species in U.S. patent application Ser. No. 13/373,424.

FEDERALLY SPONSORED RESEARCH

Not Applicable

SEQUENCE LISTING OR PROGRAM

Not Applicable

BACKGROUND

Field of Invention

This invention relates to the field of endovascular stents.

Introduction to Cerebral Aneurysms

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain.

Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function.

Review of Aneurysm Clipping and Coiling

Surgical clipping ("clipping") of cerebral aneurysms is a long-established means of treatment. Clipping involves clamping a clip on the aneurysm neck from outside the blood vessel. This stops blood flow to the aneurysm so that the aneurysm embolizes and stops growing. Aneurysm clipping is relatively invasive surgery that generally includes a craniotomy with temporary removal of a section of the skull. Aneurysm clips are generally metal.

Aneurysm clipping was developed during the 1930's and is well-established as a method of treating cerebral aneurysms, particularly aneurysms that have ruptured and are bleeding. However, the use of aneurysm clipping is decreasing, particularly in Europe, due to the development of less-invasive endovascular methods such as coils and stents. There are many aneurysm clips in the prior art, but we have not categorized or reviewed them herein because the primary focus of this disclosure is on specialized neurovascular stents which are an alternative to surgical clipping for treating cerebral aneurysms.

There are limitations of surgical clipping for treatment of cerebral aneurysms. For example, there are health risks such as infection and body stress that are generally associated with major surgery. Major surgery is also associated with relatively long recovery periods and significant costs of care. Due to the invasive nature of the operation, there is also a risk of injury to other brain tissue during the surgery. Also, the aneurysm neck can be pinched or (further) ruptured. Even with removal of a section of the skull and the best surgical practices, it can still be difficult to access some deep areas of the brain. It is often difficult to surgically clip fusiform aneurysms. Finally, clipping the aneurysm neck from outside the vessel fails to address any hemodynamic problems within the parent vessel that contributed to the formation of the aneurysm in the first place.

In response to these limitations of surgical clipping, less-invasive endovascular alternatives to surgical clipping have been developed during the past three decades. These endovascular approaches have evolved from implanting balloons within the aneurysm, to inserting flexible embolic coils into the aneurysm ("coiling"), to inserting metal coils into the aneurysm accompanied by a stent in the parent vessel ("stent-assisted coiling" or "jailing"), to specialized neurological stents that reconstruct the parent vessel and may be used as stand-alone therapy without coils.

Of these endovascular alternatives to clipping, coiling is the most established. Embolic coils are delivered into the aneurysm through an endovascular catheter and then released into the aneurysm in a series of relatively-random loops. These coils do not completely fill the volume of the aneurysm. Coiling seeks to fill a sufficient percentage of the volume of the aneurysm (the "packing density") such that the flow of blood is reduced. Then the interior matter of the aneurysm embolizes and vessel wall cells grow over the aneurysm neck.

Endovascular aneurysm coiling was developed in the early 1990's by Guido Guglielmi at UCLA. Historically, most aneurysm coils have been metal, primarily platinum. However, coils can also be made from other materials such as polymers and hydrogels. Coiling is less invasive than clipping and is associated with shorter recovery periods. Coiling is more common in Europe than in the U.S. There are many aneurysm coils in the prior art, but we have not categorized or reviewed them in depth herein because the primary focus of this disclosure is on specialized neurovascular stents which are an alternative (or adjunctive device) to coiling.

Although coiling is well-established in the treatment of cerebral aneurysms, it still has several limitations. Coils generally fill only a limited percentage of the volume ("packing density") of the aneurysm. Although there is considerable variation in packing density, some studies show that less than 50% of procedures achieve complete angiographic occlusion in follow-up evaluation. Lower occlusion is associated with a higher risk of recanalization and rupture. Coils can also compact over time, which can lead to recanalization. Recanalization rates can be in the range of 30%-50%. Gaps between coils in the region of the aneurysm neck can allow persistent inflow and continued aneurysm growth. It is difficult to treat wide-neck or fusiform aneurysm with coils, especially unaccompanied by a specialized stent.

Among the other limitations of coiling, coils can prolapse through the aneurysm neck into the parent vessel during or after the procedure. Also, it is difficult to clip an aneurysm that has been filled with metal coils, if needed later, because a clip around the coils in the sac can cause the sac to rupture. Coils can also put undesirable pressure on surrounding brain tissue; this is called the "mass effect". There is a risk that coils, especially metal coils, can puncture the aneurysm wall. Coils, especially those made with platinum, can be expensive. Clots from the aneurysm can escape into the parent vessel and cause a downstream stroke during coiling. Finally, as with surgical clipping, coils alone do not correct any hemodynamic problems in the parent vessel that contributed to the formation of the aneurysm in the first place. In the latter case, the aneurysm may continue to grow after coiling.

Despite the options of surgical clipping and endovascular coiling for treating cerebral aneurysms, these methods still have significant limitations as discussed above. Cerebral aneurysms still cause significant mortality and morbidity. Accordingly, there is still a significant clinical need for better devices and methods to treat cerebral aneurysms. This is especially true for wide-neck aneurysms and aneurysms that are located near branching vessels. Towards this end, there is ongoing work toward the development of specialized neurovascular stents to address the problems of clipping and coiling, either as a stand-alone treatment or in combination with coils. As we will discuss later in this disclosure, our present invention is an innovative type of neurovascular stent that can provide better treatment of cerebral aneurysms, especially wide-neck aneurysms and aneurysms near branching vessels. In preparation for this disclosure, we now provide a review and categorization of stent technology in the prior art (including, but not limited to, neurovascular stents) with a particular focus on the need for stents with differential wall porosity to treat aneurysms near branching vessels.

Review of Endovascular Stents

It is a challenging task to try to classify the prior art concerning stents. There are hundreds of examples of relevant prior art. However, classification of the prior art into discrete categories, even if imperfect, is an invaluable tool for reviewing the prior art, identifying the limitations of the prior art, and setting the stage for discussion of the advantages of the present invention in subsequent sections. Accordingly, we have created a classification scheme for relevant stents in the prior art and used this scheme to organize our review of the prior art. It should be noted that some portions of our discussion of the limitations of the prior art point beyond that which would be obvious from the prior art. This sets the stage for later discussion of how our present invention addresses unmet clinical needs.

There are different ways in which one might classify stent technology in the prior art. Our classification scheme has a particular focus on the porosity of the stent wall. We highlight the means, timing, and location wherein stents may be configured with differential wall porosity. Of particular interest is the extent to which stents in the prior art do, or do not, allow in situ adjustment of stent wall porosity after insertion of the stent into the parent vessel of an aneurysm. This is especially important for treating aneurysms near branching vessels and is a key feature of the invention that we will disclose later in this document.

Towards this end, our classification scheme starts with three major stent categories based on the timing and location (pre-insertion, in situ after insertion, and in situ after expansion) of stent configuration. This scheme then sub-divides these major categories into specific categories based on stent configuration specifics. For each category, we discuss key attributes of devices in that category, discuss key limitations of devices in that category, and then identify examples of prior art which appear to fit within that category.

The three major stent categories in this classification are: [a] stents with pre-insertion determination of post-expansion configuration; [b] stents with in situ (post-insertion, pre-expansion) determination of post-expansion configuration; and [c] stents with in situ (post-expansion) determination of configuration. We also include a fourth category [d] for other art that is potentially relevant, but does not fall neatly into one of these three major categories. Examples of other potentially-relevant art include Micro Electrical Mechanical Systems (MEMS), shape memory materials, and complex multi-chambered balloons. In total, approximately 350 examples of prior art are included in this review.

Sub-division of these three major categories yields the following specific categories: [a1] stents with pre-insertion determination of uniform intermediate porosity, [a2] stents with pre-insertion determination of longitudinal variation in wall flexibility or strength, [a3] stents with pre-insertion determination of longitudinal taper (or other longitudinal variation in cross-sectional size or shape), [a4] stents with pre-insertion determination of asymmetric cross-sectional perimeter, [a5] stents with pre-insertion determination of a solid (convex) area on wall, [a6] stents with pre-insertion determination of an open (convex) hole in wall, [a7] stents with pre-insertion determination of a low or high porosity (ring) segment along wall, and [a8] stents with pre-insertion determination of a low or high porosity (convex) area on wall; [b1] stents with in situ (post-insertion, pre-expansion) determination of length, [b2] stents with in situ (post-insertion, pre-expansion) determination of multiple stent delivery, [b3] stents with in situ (post-insertion, pre-expansion) determination of longitudinal axis curvature, [b4] stents with in situ (post-insertion, pre-expansion) determination of longitudinal taper (or other longitudinal variation in cross-sectional size or shape), [b5] stents with in situ (post-insertion, pre-expansion) determination of asymmetric cross-sectional perimeter, and [b6] stents with in situ (post-insertion, pre-expansion) determination of a low or high porosity (ring) segment along wall; [c1] stents with in situ (post-expansion) determination of a low or high porosity (ring) segment along wall and [c2] stents with in situ (post-expansion) determination of a low or high porosity (convex) area on wall; and [d1] stents with Micro Electro Mechanical Systems (MEMS), [d2] stents with shape memory materials, [d3] complex balloon configurations, and [d4] unclassified but potentially-relevant prior art.

A. Stents with Pre-Insertion Determination of Post-Expansion Configuration

A1. Stents with Pre-Insertion Determination of Uniform Intermediate Porosity

Stents in this category have an intermediate level of post-expansion wall porosity that is substantially uniform over the entire stent wall. For stents in this category, apart from whatever adjustment of uniform post-expansion porosity can be achieved by adjusting the stent's post-expansion diameter, this uniform level of porosity cannot be adjusted after stent has been inserted into the body. Since the post-expansion stent diameter has to fit the diameter of the parent vessel, the user has little effective control over post-expansion porosity in situ. When stents in this category are used to treat a cerebral aneurysm near branching vessels, the intent is that the stent have a wall porosity that is low enough to reduce blood flow into the aneurysm, but high enough to allow blood flow to the branching vessels. This is a tough balancing act. Depending on the configuration of the aneurysm and branching vessels, these conflicting objectives can be difficult, or impossible, to achieve with a stent with uniform wall porosity. Stents in this category can be superior to conventional uniformly-high-porosity stents (in terms of reducing blood flow to the aneurysm) and can be superior to conventional uniformly-low-porosity stents (such as impermeable stent grafts), but their "one porosity fits all" design causes a number of limitations for treating cerebral aneurysms.

Limitations of stents with pre-insertion determination of uniform intermediate porosity include the following. When such stents are used to contain coils, a solidifying mass of liquid, or other embolic materials within the aneurysm, then their intermediate level of wall porosity may not have sufficiently low porosity to prevent the embolic materials from slipping or seeping out into the parent vessel. This can cause stroke. Without special wall features for coil delivery, it may be difficult to deliver coils through the stent wall into the aneurysm. Also, even though such stents allow more blood flow into nearby branching vessels than is allowed by impermeable stent grafts, this flow can still be unacceptably low. This can cause damage to brain tissue. Another potential problem with such stents is inadequate blocking of blood flow to aneurysm. This can lead to recanalization and continued aneurysm growth. Due to their uniform post-expansion wall porosity, stents in this category offer no ability to selectively adjust different areas (longitudinal or cross-sectional perimeter) of the stent wall in situ (after insertion of the stent into the parent vessel). Stent diameter can also be an issue, especially for self-expanding stents. It can be difficult to accurately assess vessel diameter and shape before the stent is actually placed within in the vessel. If the stent diameter turns out to too large, then it can injure the stent wall and cause flow problems. If the stent diameter turns out to be too small, then the stent can migrate away from the aneurysm neck and cause flow problems.

Examples of prior art that appear to fit within this category include: U.S. Pat. No. 6,342,068 (Thompson, 2002, "Three-Dimensional Braided Stent"); U.S. Pat. No. 7,052,513 (Thompson, 2006, "Three-Dimensional Braided Covered Stent"); U.S. Pat. No. 7,211,109 (Thompson, 2007, "Braided Composite Prosthesis"); U.S. Pat. No. 7,306,624 (Yodfat et al., 2007, "Implantable Intraluminal Device and Method of Using Same in Treating Aneurysms"); U.S. Pat. No. 7,572,290 (Yodfat et al., 2009, "Implantable Intraluminal Device and Method of Using Same in Treating Aneurysms"); and U.S. Pat. No. 7,942,925 (Yodfat et al., 2011, "Implantable Intraluminal Device and Method of Using Same in Treating Aneurysms"); as well as U.S. patent applications 20030100945 (Yodfat et al., 2003, "Implantable Intraluminal Device and Method of Using Same in Treating Aneurysms"); 20070219619 (Dieck et al., 2007, "Partially Covered Stent Devices and Methods of Use"); 20070239261 (Bose et al., 2007, "Aneurysm Occlusion System and Method"); and 20080039933 (Yodfat et al., 2008, "Implantable Intraluminal Device and Method of Using Same in Treating Aneurysms").

A2. Stents with Pre-Insertion Determination of Longitudinal Variation in Wall Flexibility or Strength Stents in this category are characterized by variation in wall flexibility or strength, especially along their longitudinal axis. Conceptually, such variable flexibility can be added to stents with other design features, including variation in wall porosity. However, since the primary focus of this classification scheme is on differential wall porosity, we have placed stents with advanced approaches to variation in wall porosity in other categories. The stents that we place in this category have pre-insertion determination of longitudinal variation in wall flexibility or strength, but no advanced approaches for variation in wall porosity. Stents in this category have variation in flexibility or strength along their longitudinal axis. This can be useful for navigation and deployment in curved, tapered, or generally tortuous neurovascular blood vessels for which general stents can be too stiff. However, without other special design characteristics, such stents have a number of limitations if used to treat cerebral aneurysms.

Limitations of stents with pre-insertion determination of longitudinal variation in wall flexibility or strength (but no other special design characteristics) can include the following. Their high flexibility can be correlated with relatively high wall porosity or unintentional variation in wall porosity. High wall porosity can allow continued blood flow into an aneurysm. This can result in continued growth and rupture of the aneurysm. This can also allow blood clots (or embolic materials) to escape out of the aneurysm into the parent vessel. Stents in this category do not provide any ability to selectively adjust wall porosity in situ (after insertion of the stent into the parent vessel). For example, these stents do not allow a user to decrease wall porosity in the area of the stent near the aneurysm neck or increase wall porosity in areas of the stent that cover nearby branching vessels. Stent diameter can also be an issue, particularly for flexible self-expanding stents, because it can be difficult to accurately assess vessel size before the stent is actually inserted into the vessel.

Examples of prior art that appear to fit within this category include: U.S. Pat. No. 5,836,966 (St. Germain, 1998, "Variable Expansion Force Stent"); U.S. Pat. No. 5,868,780 (Lashinski et al., 1999, "Stents for Supporting Lumens in Living Tissue"); U.S. Pat. No. 6,468,302 (Cox et al., 2002, "Variable Strength Stent"); U.S. Pat. No. 6,485,509 (Killion et al., 2002, "Stent Having Variable Properties and Method of its Use"); U.S. Pat. No. 6,558,414 (Layne, 2003, "Partial Encapsulation of Stents Using Strips and Bands"); U.S. Pat. No. 6,585,758 (Chouinard et al., 2003, "Multi-Section Filamentary Endoluminal Stent"); U.S. Pat. No. 6,602,284 (Cox et al., 2003, "Variable Strength Stent"); U.S. Pat. No. 6,610,087 (Zarbatany et al., 2003, "Endoluminal Stent Having a Matched Stiffness Region and/or a Stiffness Gradient and Methods for Providing Stent Kink Resistance"); U.S. Pat. No. 6,652,576 (Stalker, 2003, "Variable Stiffness Stent"); U.S. Pat. No. 6,669,723 (Killion et al., 2003, "Stent Having Variable Properties and Method of its Use"); U.S. Pat. No. 6,805,706 (Solovay et al., 2004, "Stent-Graft with Rails"); U.S. Pat. No. 7,001,422 (Escamilla et al., 2006, "Expandable Stent and Delivery System"); and U.S. Pat. No. 7,060,091 (Killion et al., 2006, "Stent Having Variable Properties and Method of Its Use").

Examples that appear to fit within this category also include: U.S. Pat. No. 7,112,216 (Gregorich, 2006, "Stent with Tapered Flexibility"); U.S. Pat. No. 7,309,351 (Escamilla et al., 2007, "Expandable Stent with Markers and Stent Delivery System"); U.S. Pat. No. 7,402,169 (Killion et al., 2008, "Stent Having Variable Properties and Method of its Use"); U.S. Pat. No. 7,527,644 (Mangiardi et al., 2009, "Stent with Geometry Determinated Functionality and Method of Making the Same"); U.S. Pat. No. 7,547,321 (Silvestri et al., 2009, "Removable Stent and Method of Using the Same"); U.S. Pat. No. 7,637,942 (Mangiardi et al., 2009, "Coated Stent with Geometry Determinated Functionality and Method of Making the Same"); U.S. Pat. No. 7,780,719 (Killion et al., 2010, "Stent Having Variable Properties and Method of its Use"); U.S. Pat. No. 7,935,142 (Gregorich, 2011, "Stent with Tapered Flexibility"); and U.S. Pat. No. 7,959,671 (Mangiardi et al., 2011, "Differential Covering and Coating Methods"); as well as U.S. patent application 20030074056 (Killion et al., 2003, "Stent Having Variable Properties and Method of its Use").

A3. Stents with Pre-Insertion Determination of Longitudinal Taper (or Other Longitudinal Variation in Cross-Sectional Size or Shape)

Stents in this category are designed to be tapered (or to have other longitudinal variation in post-expansion cross-sectional size or shape). This can be an advantage for placing stents in tapered blood vessels or in vessels with other types of longitudinal variation in cross-sectional size or shape. Without such longitudinal variation, a stent with a uniform post-expansion diameter that is placed in a tapered vessel can exert too much pressure on the narrower sections of the blood vessel wall (causing distension or vessel injury) and have gaps between the stent and the wider sections of the blood vessel wall (causing possible slippage or thrombogenic flow eddies). Stents in this category often expand to a narrower diameter at their distal end and a wider diameter at their proximal end. In this category, post-expansion longitudinal variation is determined by the structure of the stent before the stent is inserted into the body and is not adjustable in situ. For the purposes of this classification system, we include stents in this category that have pre-insertion longitudinal variation, but do not have advanced capabilities for selective variation of wall porosity. The latter are placed in subsequent categories.

While such tapered stents are very useful for stenting tapered vessels for other purposes, they have limitations for treating cerebral aneurysms. When a stent has a special configuration (such as a taper) that is determined before the stent is inserted into the parent vessel, there can be inaccuracies in size or shape. Even if the size and shape of the stent are completely accurate for the intended vessel, due to the tortuous nature of intracranial blood vessels it can be challenging to accurately position the stent into the precise longitudinal and rotational configurations. For example, most guidewires have distal end curvature in order to navigate tortuous vessels. Accordingly, it is difficult to independently adjust the rotational position of the stent in the vessel without shifting its longitudinal position as well. Also, particularly relevant for this disclose, the level of wall porosity is not explicitly addressed in this category. If the stent's walls are too porous, then they allow continued blood flow to the aneurysm. They may also allow blood clots or embolic materials to escape from the aneurysm. On the other hand, if the stents walls are too impermeable, then they block blood flow to branching vessels. This can cause damage to downstream areas of the brain.

Examples of prior art that appear to fit within this category include: U.S. Pat. No. 5,836,966 (St. Germain, 1998, "Variable Expansion Force Stent"); U.S. Pat. No. 5,868,780 (Lashinski et al., 1999, "Stents for Supporting Lumens in Living Tissue"); U.S. Pat. No. 5,922,019 (Hankh et al., 1999, "Conical Stent"); U.S. Pat. No. 5,938,697 (Killion et al., 1999, "Stent Having Variable Properties"); U.S. Pat. No. 6,027,526 (Limon et al., 2000, "Stent Having Varied Amounts of Structural Strength Along its Length"); U.S. Pat. No. 6,071,298 (Lashinski et al., 2000, "Stents for Supporting Lumens in Living Tissue"); U.S. Pat. No. 6,099,559 (Nolting, 2000, "Endoluminal Support Assembly with Capped Ends"); U.S. Pat. No. 6,190,406 (Duerig et al., 2001, "Intravascular Stent Having Tapered Struts"); U.S. Pat. No. 6,231,597 (Deem et al., 2001, "Apparatus and Methods for Selectively Stenting a Portion of a Vessel Wall"); U.S. Pat. No. 6,273,910 (Limon, 2001, "Stent with Varying Strut Geometry"); U.S. Pat. No. 6,475,236 (Roubin et al., 2002, "Non-Foreshortening Intraluminal Prosthesis"); U.S. Pat. No. 6,485,509 (Killion et al., 2002, "Stent Having Variable Properties and Method of its Use"); U.S. Pat. No. 6,569,193 (Cox et al., 2003, "Tapered Self-Expanding Stent"); U.S. Pat. No. 6,579,314 (Lombardi et al., 2003, "Covered Stent with Encapsulated Ends"); U.S. Pat. No. 6,585,753 (Eder et al., 2003, "Expandable Coil Stent"); and U.S. Pat. No. 6,610,087 (Zarbatany et al., 2003, "Endoluminal Stent Having a Matched Stiffness Region and/or a Stiffness Gradient and Methods for Providing Stent Kink Resistance").

Examples that appear to fit within this category also include: U.S. Pat. No. 6,652,576 (Stalker, 2003, "Variable Stiffness Stent"); U.S. Pat. No. 6,669,723 (Killion et al., 2003, "Stent Having Variable Properties and Method of its Use"); U.S. Pat. No. 7,033,385 (Eder et al., 2006, "Expandable Coil Stent"); U.S. Pat. No. 7,052,510 (Richter, 2006, "Two Balloon Staged Stent Expansion"); U.S. Pat. No. 7,060,091 (Killion et al., 2006, "Stent Having Variable Properties and Method of Its Use"); U.S. Pat. No. 7,241,308 (Andreas et al., 2007, "Stent Deployment Systems and Methods"); U.S. Pat. No. 7,288,112 (Denardo et al., 2007, "Intravascular Flow Modifier and Reinforcement Device"); U.S. Pat. No. 7,309,352 (Eder et al., 2007, "Expandable Coil Stent"); U.S. Pat. No. 7,402,169 (Killion et al., 2008, "Stent Having Variable Properties and Method of its Use"); U.S. Pat. No. 7,491,229 (Eder et al., 2009, "Expandable Coil Stent"); U.S. Pat. No. 7,527,644 (Mangiardi et al., 2009, "Stent with Geometry Determinated Functionality and Method of Making the Same"); U.S. Pat. No. 7,547,321 (Silvestri et al., 2009, "Removable Stent and Method of Using the Same"); U.S. Pat. No. 7,780,719 (Killion et al., 2010, "Stent Having Variable Properties and Method of its Use"); U.S. Pat. No. 7,862,608 (Hogendijk et al., 2011, "Vascular Prosthesis and Methods of Use"); and U.S. Pat. No. 7,918,881 (Andreas et al., 2011, "Stent Deployment Systems and Methods").

Examples that appear to fit within this category also include: U.S. patent applications 20030074056 (Killion et al., 2003, "Stent Having Variable Properties and Method of its Use"); 20040249435 (Andreas et al., 2004, "Stent Deployment Systems and Methods"); 20040249439 (Richter et al., 2004, "Method and Apparatus for Stenting"); 20050119684 (Guterman et al., 2005, "Aneurysm Buttress Arrangement"); 20060058864 (Schaeffer et al., 2006, "Balloon Flareable Branch Vessel Prosthesis and Method"); 20060085061 (Vardi et al., 2006, "Extendible Stent Apparatus and Method for Deploying the Same"); 20090132028 (Vardi et al., 2009, "Extendible Stent Apparatus and Method for Deploying the Same"); 20100042200 (Richter et al., 2010, "Method and Apparatus for Stenting"); and 20100228338 (Thompson, 2010, "Stents with Tapered Struts").

A4. Stents with Pre-Insertion Determination of Asymmetric Cross-Sectional Perimeter Stents in this category have one or more cross-sectional perimeters that are radially asymmetric after expansion. There do not appear to be many examples of such stents in the prior art. Such stents can be useful for cross-sectional vessels that are radially asymmetric. In theory, they could also be useful for vessels that have symmetric cross-sections, but for which one part of a cross-sectional perimeter spans an aneurysm and another part of the same perimeter spans the entrance to a branching vessel. For example, the latter can occur when there is an entrance to a branching vessel that is on the other side of a parent vessel across from the neck of an aneurysm. However, it should be noted that having a stent with an asymmetric cross-sectional perimeter shape is not the same as having a stent with differential cross-sectional perimeter porosity. For example, a stent cross-section may have a circular perimeter shape, but have differences in porosity around that circular perimeter. Also, a stent cross-section may have an irregular perimeter shape, but have uniform porosity around that irregular perimeter. Ideally, one would want control of differential cross-sectional porosity, not just differential cross-sectional size.

Stents in this category have their post-expansion cross-sectional asymmetric shape determined prior to insertion. It is not adjustable in situ. This is due to the way in which they are constructed. Due to imprecision in imaging and stent shape customization, it can be challenging to create a stent whose shape irregularities will accurately match the shape irregularities of a parent vessel after the stent is expanded in the blood vessel. Even if the shape is perfectly matched to the parent vessel, accurate longitudinal and rotational positioning of the stent in the parent vessel can be challenging in tortuous vessels. If the stent is not a good fit or is not accurately positioned, then the intended benefits of custom asymmetric design will not be realized. In this respect, it would be preferable to have a stent whose configuration can be adjusted in situ based on the stent's actual longitudinal and rotational placement within the parent vessel.

There are other potential limitations of using such stents for treatment of cerebral aneurysms. Differential cross-sectional shape does not ensure sufficiently low porosity to block blood flow to the aneurysm neck. Neither does it ensure sufficiently high porosity to allow blood flow to nearby branching vessels. Also, there are no unique design features that guard against blood clots or embolic materials leaking out from the aneurysm. An asymmetric cross-sectional perimeter may cause gaps between the stent wall and the aneurysm neck that could increase the risk of blood clots or embolic materials leaking out from the aneurysm. This stent design does not guarantee a tight fit with low-porosity over the aneurysm neck. As mentioned above, it can be difficult to accurately configure a stent before insertion into the blood vessel and to accurately position it within the blood vessel to match the configuration of the vessel. It would be advantageous to have a stent that can be configured in situ. Examples of prior art that appear to fit within this category include U.S. Pat. No. 7,722,657 (Hartley, 2010, "Asymmetric Stent Graft Attachment") and U.S. patent application 20100042200 (Richter et al., 2010, "Method and Apparatus for Stenting").

A5. Stents with Pre-Insertion Determination of Solid (Convex) Area on Wall

Stents in this category are constructed, prior to insertion, with one or more wall areas that are pre-determined to be substantially impermeable after expansion. An impermeable wall area may be circular, saddle-shaped, ring-shaped, or some other shape. Usually, this shape is convex. For example, the stent may be a generally high-porosity tubular-shaped stent that has a saddle-shaped blood-impermeable area on its wall after expansion. This saddle-shaped low-porosity area may be intended to be positioned over the neck of an aneurysm when the stent is deployed in order to occlude blood flow to the aneurysm. The remaining area of the stent wall, being generally high-porosity, is intended to allow blood flow to nearby branching vessels.

Such stents have the potential to be effective for blocking blood flow to a cerebral aneurysm while allowing blood flow to nearby branching vessels. However, the success of these stents for treating cerebral aneurysms depends on: creating a stent with the proper post-expansion configuration; and then successfully deploying that stent in the right position to selectively block the aneurysm neck. Ideally, the stent should block blood flow to the aneurysm, but allow blood flow to branching vessels. This can be challenging. It can be difficult to accurately assess the size and configuration of a tortuous vessel from outside the body using remote imaging. Also, it can be challenging to create a stent with a wall area that remains solid when expanded. Expandable meshes generally become more porous when expanded. Impermeable graft patches have to be unfolded or stretched out.

Even if a stent can be created with a configuration that would match the parent vessel perfectly, it can be challenging to align it, both longitudinally and rotationally, within the parent vessel in tortuous anatomy. Guidewires and catheters often have curved distal ends, making it challenging to independently adjust longitudinal placement and rotational placement. For these reasons, although differential wall porosity is a great concept for treating cerebral aneurysms, it would be advantageous to have a stent that allows users to determine differential wall porosity in situ. This could allow in situ creation of a low-porosity area right over the neck of the aneurysm based on the way that the stent is actually placed within the parent vessel. Flexibility can also be an issue for stents with pre-insertion determination of a solid area on the wall, especially since grafts and solid neck patches can lack the flexibility needed to navigate tortuous intracranial vessels.

Examples of prior art that appear to fit within this category include: U.S. Pat. No. 6,007,573 (Wallace et al., 1999, "Intracranial Stent and Method of Use"); U.S. Pat. No. 6,139,564 (Teoh, 2000, "Minimally Occlusive Flow Disruptor Stent for Bridging Aneurysm Necks"); U.S. Pat. No. 6,309,367 (Boock, 2001, "Aneurysm Shield"); U.S. Pat. No. 6,605,111 (Bose et al., 2003, "Endovascular Thin Film Devices and Methods for Treating and Preventing Stroke"); U.S. Pat. No. 7,232,461 (Ramer, 2007, "Neck Covering Device for an Aneurysm"); U.S. Pat. No. 7,621,928 (Thramann et al., 2009, "Aneurysm Stent"); U.S. Pat. No. 7,901,445 (Wallace et al., 2011, "Intracranial Stent and Method of Use"); and U.S. Pat. No. 8,038,706 (Eidenschink et al., 2011, "Crown Stent Assembly"); as well as U.S. patent applications 20070219610 (Israel, 2007, "Stent with Flap"); 20070225794 (Thramann et al., 2007, "Aneurysm Stent"); 20090069880 (Vonderwalde et al., 2009, "Implantable Graft Assembly and Aneurysm Treatment"); 20100106240 (Duggal et al., 2010, "Systems and Methods for Aneurysm Treatment and Vessel Occlusion"); 20110022149 (Cox et al., 2011, "Methods and Devices for Treatment of Vascular Defects"); and 20110160833 (Gonzalez et al., 2011, "Implantable Graft Assembly").

A6. Stents with Pre-Insertion Determination of Open (Convex) Hole in Wall

Stents in this category are created to have a hole in their wall after they are expanded. Generally, the idea is to place the hole over the entrance to a branching or forked vessel in order to allow continued blood flow to that vessel despite an overall low-porosity stent wall. The hole is sometimes connected to a second stent, a branching stent, or a second component of the same stent, so that the result is a branching or forked stent design. Such stents are relatively common for treatment of Aortic Abdominal Aneurysms (AAA's), but the concept can also be useful for occluding cerebral aneurysms in neurovascular areas with branches such the Circle of Willis. Particularly in tortuous vessels, the precise configuration and positioning of holes can be difficult. In this category, the location of the hole is determined prior to the insertion of the stent into the blood vessel rather than in situ. In some respects, stents in this category are the inverse of stents in the previous category that have pre-insertion determination of a post-expansion solid area on the stent wall. However, the relationship is not completely inverse. For example, "expanding a hole" from pre-expansion to post-expansion stent configuration is less complicated than "expanding a solid patch."

The main focus of stents in this category is on maintaining blood flow to a branching or forked blood vessel. Successful occlusion of the aneurysm neck is not explicitly addressed. It may be assumed that the rest of the stent has sufficiently low-porosity walls that it blocks blood flow to the aneurysm, but this is not as simple as it sounds. Using expanding meshes, it can be challenging to accumulate enough wall mass over the aneurysm neck in the post-expansion configuration of the stent to successfully block blood flow. Using stent liners or graph patches can offer more concentrated mass over the aneurysm neck, but can be insufficiently flexible to navigate through tortuous vessels. As with other stents with special configurations that are determined prior to insertion within the parent vessel, inaccuracies in shape or placement will interfere with the intended functioning of the stent. It would be advantageous to have a stent wherein the location of one or more wall holes can be determined in situ, after insertion of the stent into the vessel. It would also be advantageous to have a stent with an explicit mechanism for accumulating sufficient wall mass over the aneurysm neck to assure proper occlusion without the need for a solid stent liner or graft.

Examples of prior art that appear to fit within this category include: U.S. Pat. No. 5,723,004 (Dereume et al., 1998, "Expandable Supportive Endoluminal Grafts"); U.S. Pat. No. 5,948,018 (Dereume et al., 1999, "Expandable Supportive Endoluminal Grafts"); U.S. Pat. No. 6,030,414 (Taheri, 2000, "Variable Stent and Method for Treatment of Arterial Disease"); U.S. Pat. No. 6,129,754 (Kanesaka et al., 2000, "Stent for Vessel with Branch"); U.S. Pat. No. 6,159,238 (Killion et al., 2000, "Stent Having Variable Properties and Method of Its Use"); U.S. Pat. No. 6,165,212 (Dereume et al., 2000, "Expandable Supportive Endoluminal Grafts"); U.S. Pat. No. 6,210,429 (Vardi et al., 2001, "Extendible Stent Apparatus"); U.S. Pat. No. 6,309,413 (Dereume et al., 2001, "Expandable Supportive Endoluminal Grafts"); U.S. Pat. No. 6,312,463 (Rourke et al., 2001, "Micro-Porous Mesh Stent with Hybrid Structure"); U.S. Pat. No. 6,395,018 (Castaneda, 2002, "Endovascular Graft and Process for Bridging a Defect in a Main Vessel Near One of More Branch Vessels"); U.S. Pat. No. 6,599,316 (Vardi et al., 2003, "Extendible Stent Apparatus"); U.S. Pat. No. 6,676,701 (Rourke et al., 2004, "Micro-Porous Mesh Stent with Hybrid Structure"); and U.S. Pat. No. 6,835,203 (Vardi et al., 2004, "Extendible Stent Apparatus").

Examples that appear to fit within this category also include: U.S. Pat. No. 6,962,602 (Vardi et al., 2005, "Method for Employing an Extendible Stent Apparatus"); U.S. Pat. No. 6,994,721 (Israel, 2006, "Stent Assembly"); U.S. Pat. No. 7,029,492 (Mitsudou et al., 2006, "Implanting Stent and Dilating Device"); U.S. Pat. No. 7,041,129 (Rourke et al., 2006, "Micro-Porous Mesh Stent with Hybrid Structure"); U.S. Pat. No. 7,186,263 (Golds et al., 2007, "Mesh Graft and Stent for Increased Flexibility"); U.S. Pat. No. 7,413,573 (Hartley et al., 2008, "Fenestrated Stent Grafts"); U.S. Pat. No. 7,537,609 (Davidson et al., 2009, "Extendible Stent Apparatus"); U.S. Pat. No. 7,645,298 (Hartley et al., 2010, "Stent Graft Fenestration"); U.S. Pat. No. 7,695,509 (Rourke et al., 2010, "Micro-Porous Mesh Stent with Hybrid Structure"); U.S. Pat. No. 7,766,955 (Vardi et al., 2010, "Extendible Stent Apparatus"); U.S. Pat. No. 7,823,263 (Wu, 2010, "Method of Removing Stent Islands from a Stent"); U.S. Pat. No. 7,850,725 (Vardi et al., 2010, "Extendible Stent Apparatus"); U.S. Pat. No. 7,892,279 (Davidson et al., 2011, "Extendible Stent Apparatus"); U.S. Pat. No. 7,901,445 (Wallace et al., 2011, "Intracranial Stent and Method of Use"); and U.S. Pat. No. 8,016,878 (Meyer et al., 2011, "Bifurcation Stent Pattern").

Other examples that also appear to fit within this category include: U.S. patent applications: 20010016766 (Vardi et al., 2001, "Extendible Stent Apparatus"); 20010037137 (Vardi et al., 2001, "Extendible Stent Apparatus"); 20020116047 (Vardi et al., 2002, "Extendible Stent Apparatus and Method for Deploying the Same"); 20020156516 (Vardi et al., 2002, "Method for Employing an Extendible Stent Apparatus"); 20030074049 (Hoganson et al., 2003, "Covered Stents and Systems for Deploying Covered Stents"); 20040015227 (Vardi et al., 2004, "Extendible Stent Apparatus"); 20040111142 (Rourke et al., 2004, "Micro-Porous Mesh Stent with Hybrid Structure"); 20050131518 (Hartley et al., 2005, "Fenestrated Stent Grafts"); 20050149166 (Schaeffer et al., 2005, "Branch Vessel Prosthesis with Anchoring Device and Method"); 20050171597 (Boatman et al., 2005, "Helical Stent for Branched Vessel Prosthesis"); 20050171598 (Schaeffer, 2005, "Aorta and Branch Vessel Stent Grafts and Method"); 20050222668 (Schaeffer et al., 2005, "Flareable Branch Vessel Prosthesis and Method"); 20060241740 (Vardi et al., 2006, "Extendible Stent Apparatus"); 20070179592 (Schaeffer, 2007, "Branch Vessel Prosthesis with Positional Indicator System and Method"); 20070299498 (Perez et al., 2007, "Methods and Devices for Aiding In Situ Assembly of Repair Devices"); 20080215018 (Duffy et al., 2008, "Method and Apparatus for Treating Stenoses at Bifurcated Regions"); 20080312732 (Hartley et al., 2008, "Fenestrated Stent Grafts"); 20090171437 (Brocker et al., 2009, "Low Profile Non-Symmetrical Stent"); 20090306763 (Roeder. et al., 2009, "Low Profile Non-Symmetrical Bare Alignment Stents with Graft"); 20100161026 (Brocker et al., 2010, "Low Profile Non-Symmetrical Stent"); 20100312326 (Chuter et al., 2010, "Apparatus and Methods for Deployment of a Modular Stent-Graft System"); 20110082533 (Vardi et al., 2011, "Extendible Stent Apparatus"); and 20110224774 (Silveira

A7. Stents with Pre-Insertion Determination of Low or High Porosity (Ring) Segment Along Wall This is the first category of stents that explicitly offer users some control over differences in porosity across different wall areas. In this category, these differences in wall porosity are determined before the stent is inserted into the blood vessel. They are not determined in situ. As mentioned previously, variation in wall porosity is not the same as variation in wall shape. Two different stents can have the same shape walls, but different wall porosities. Also, two different stents can have similar wall porosities, but different wall shapes. When it comes to selectively blocking blood flow to an aneurysm, but allowing blood flow to nearby branching vessels, one can seek to accomplish this by varying wall shape, wall porosity, or both. Of the two approaches, variation in wall porosity is a more direct approach because porosity relates more directly to blocking vs. enabling blood flow.

Stents in this category have differences in wall porosity along different segments (thick "rings") along the length of the stent. The goal is to position a low-porosity segment of the stent over the aneurysm neck and to position a high-porosity segment of the stent over the entrance to any nearby branching vessel. There may be multiple high-porosity segments if there are multiple branching vessels nearby. This configuration only works properly if the aneurysm neck and the entrances to the branching vessel are not diametrically opposite each other—that is, if they are not in the same cross-sectional perimeter of the stent. Otherwise, the neck and branch are covered by the same uniform-porosity ring.

As one example of a stent in this category, a tubular-shaped stent may be created with a low-porosity center section. The intention is to span the neck of the aneurysm with the center section. The stent may also have high-porosity distal and proximal end sections that are intended to span nearby branching vessels. If there were a branching vessel diametrically opposite the aneurysm neck, then this would not work because the central low-porosity section would block blood flow to that branching vessel. As with other stents whose non-uniform structure is created prior to insertion within the blood vessel, successful use of a stent like this depends on: creating a stent with a configuration that accurately matches the configuration of the parent vessel; and successful longitudinal and rotational positioning of that stent within that vessel. As mentioned previously, it can be difficult to assess the precise configuration of a vessel from external imaging before insertion of the stent into the vessel. Even if this can be done accurately, it can be challenging to position the stent so that the aneurysm neck is occluded but branching vessels are not. With distally-curved guidewires and catheters, longitudinal movement and rotational movement may not be independently controllable. For these reasons, it would be advantageous to have a stent wherein variation in wall porosity can be selectively adjusted in situ.

Another potential limitation of stents with pre-insertion determination of a low or high porosity (ring) segment along its wall is that it can be difficult to concentrate enough wall mass, post-expansion, in the vicinity of the aneurysm neck to successfully occlude the aneurysm. This is especially true with uniform radial expansion. Meshes tend to have reduced porosity when expanded. Impermeable grafts, liners, and patches are alternatives to meshes, but they must be stretchable or unfolded, which poses other challenges. For these reasons, it would be advantageous to have a stent wherein wall mass can be concentrated in particular areas during the expansion process.

Examples of prior art that appear to fit within this category include: U.S. Pat. No. 5,693,088 (Lazarus, 1997, "Intraluminal Vascular Graft"); U.S. Pat. No. 5,769,884 (Solovay, 1998, "Controlled Porosity Endovascular Implant"); U.S. Pat. No. 6,270,523 (Herweck et al., 2001, "Expandable Shielded Vessel Support"); U.S. Pat. No. 6,468,302 (Cox et al., 2002, "Variable Strength Stent"); U.S. Pat. No. 6,558,414 (Layne, 2003, "Partial Encapsulation of Stents Using Strips and Bands"); U.S. Pat. No. 6,602,284 (Cox et al., 2003, "Variable Strength Stent"); U.S. Pat. No. 6,796,997 (Penn et al., 2004, "Expandable Stent"); U.S. Pat. No. 6,913,618 (Denardo et al., 2005, "Intravascular Flow Modifier and Reinforcement Device"); U.S. Pat. No. 7,112,216 (Gregorich, 2006, "Stent with Tapered Flexibility"); U.S. Pat. No. 7,226,475 (Lenz et al., 2007, "Stent with Variable Properties"); U.S. Pat. No. 7,288,112 (Denardo et al., 2007, "Intravascular Flow Modifier and Reinforcement Device"); U.S. Pat. No. 7,763,011 (Ortiz et al., 2010, "Variable Density Braid Stent"); U.S. Pat. No. 7,857,843 (Henderson, 2010, "Differentially Expanded Vascular Graft"); and U.S. Pat. No. 7,935,142 (Gregorich, 2011, "Stent with Tapered Flexibility"); as well as U.S. patent applications (Gregorich, 2004, "Stent with Tapered Flexibility"); 20040260384 (Allen, 2004, "Superelastic Coiled Stent"); 20060229714 (Lombardi et al., 2006, "Covered Stent with Encapsulated Ends"); 20070021816 (Rudin, 2007, "Stent Vascular Intervention Device and Methods for Treating Aneurysms"); 20090069880 (Vonderwalde et al., 2009, "Implantable Graft Assembly and Aneurysm Treatment"); and 20100106240 (Duggal et al., 2010, "Systems and Methods for Aneurysm Treatment and Vessel Occlusion").

A8. Stents with Pre-Insertion Determination of Low or High Porosity (Convex) Area on Wall Stents in this category are similar to those in the previous category, except that in this category there is more flexibility in the shape of the post-expansion configuration of the low-porosity or high-porosity wall areas. In the previous category, the low-porosity or high-porosity wall areas were limited to being longitudinal segments (thick "rings") along the stent wall. In this category, the shapes of the low or high porosity wall areas need not be segments. In this category, the low or high porosity areas can be circular, saddle-shaped, or some other (convex) shaped area. This increased range of wall area shapes allows these stents to be used even in cases wherein the aneurysm neck and a branching vessel are diametrically opposite each other. One portion of the perimeter of a stent cross-section can be low-porosity to cover the aneurysm neck and another portion of the perimeter of that cross-section can be high-porosity to cover the entrance to the branching vessel.

However, stents in this category are still limited because post-expansion wall porosity cannot be determined or adjusted in situ. In this category, as in previous ones, any differences in wall porosity must be determined before the stent is inserted into the vessel. Accordingly, this category shares many of the same limitations as stents in the previous category. It can be challenging determining the precise size and configuration of tortuous vessels from outside the body using remote imaging. This makes it tough to precisely configure the stent, including areas with differential wall porosity, outside the body. Even if a stent can be perfectly configured in shape and size outside the body, it can also be a challenge getting it to the precise longitudinal and rotational position within the parent vessel in a tortuous vessel.

It is tough to precisely match up low-porosity wall areas with the aneurysm neck and high-porosity areas with the entrances to branching vessels. To avoid these challenges and limitations, it would be advantageous to have a stent that gives users the ability to selectively determine low or high porosity wall areas in situ, after the stent has been positioned within the parent vessel. Such ability would mean that that the user could insert the stent into the parent vessel in virtually any rotational (or longitudinal) configuration and then configure the wall areas. Unlike stents in this category or in previous categories, a user could then create low or high porosity stent wall areas to match real-time observed structural characteristics of the vessel, such as the aneurysm neck and branching vessels.

Examples of prior art that appear to fit within this category include: U.S. Pat. No. 5,951,599 (McCrory, 1999, "Occlusion System for Endovascular Treatment of an Aneurysm"); U.S. Pat. No. 5,957,975 (Lafont et al., 1999, "Stent Having a Programmed Pattern of in Vivo Degradation"); U.S. Pat. No. 6,059,822 (Kanesaka et al., 2000, "Stent with Different Mesh Patterns"); U.S. Pat. No. 6,129,754 (Kanesaka et al., 2000, "Stent for Vessel with Branch"); U.S. Pat. No. 6,258,115 (Dubrul, 2001, "Bifurcated Stent and Distal Protection System"); U.S. Pat. No. 6,398,803 (Layne et al., 2002, "Partial Encapsulation of Stents"); U.S. Pat. No. 6,770,087 (Layne et al., 2004, "Partial Encapsulation of Stents"); U.S. Pat. No. 6,969,401 (Marotta et al., 2005, "Endovascular Prosthesis"); U.S. Pat. No. 7,231,260 (Wallace et al., 2007, "Intravascular Self-Anchoring Electrode Body with Arcuate Springs/Spring Loops/or Arms"); U.S. Pat. No. 7,491,226 (Palmaz et al., 2009, "Endoluminal Implantable Stent-Grafts"); U.S. Pat. No. 7,641,680 (Palmaz et al., 2010, "Endoluminal Implantable Stent-Grafts"); and U.S. Pat. No. 8,007,529 (Yan, 2011, "Medicated Porous Metal Prosthesis"); as well as U.S. patent applications 20030109917 (Rudin et al., 2003, "Stent Vascular Intervention Device and Method"); 20030139802 (Wulfman et al., 2003, "Medical Device"); 20080004653 (Sherman et al., 2008, "Thin Film Devices for Occlusion of a Vessel"); 20100063531 (Rudakov et al., 2010, "Medical Device with Non-Circumferential Surface Portion").

B. Stents with In Situ (Post-Insertion, Pre-Expansion) Determination of Post-Expansion Configuration In discussing the limitations of previous stent categories, we repeatedly mentioned that it would be advantageous to have a stent that gives the user the capability to adjust the configuration of the stent in situ, after insertion of the stent into the parent blood vessel. The following stent categories give the user the ability to customize the configuration of a stent in situ. One might wonder why we have further differentiated between [B category] stents whose configuration can be adjusted post-insertion, but pre-expansion, vs. [C category] stents whose configuration can be adjusted post-insertion and post-expansion. The answer is that there are means and methods of stent customization that work before stent expansion, but do not work after expansion. For example, methods of stent customization that rely on differential expansion work before expansion, but do not work after expansion because uniform expansion has already occurred. There are also means of stent customization that work after stent expansion, but do not work before expansion. For example, methods that fill in the space between an expanded stent and the vessel wall work after expansion, but do not work before expansion because they interfere with the expansion process. This is why we differentiate, in the remainder of this classification scheme, between [B category] stents with post-insertion, pre-expansion customization vs. [C category] stents with post-insertion, post-expansion customization.

B1. Stents with In Situ (Post-Insertion, Pre-Expansion) Determination of Length

This is the first category that includes stents for which certain aspects of their configuration can be adjusted in situ. For stents in this category, the aspect that can be adjusted after insertion of the stent into the vessel is their length. Giving a user the ability to determine the length of a stent after it has been inserted into the parent blood vessel is useful for reducing the variety of stents needed for inventory and for tailoring the length of the stent in situ based on observation of the stent within the vessel. In the extreme, this can avoid the time and risk involved in withdrawing a stent from the vessel that looked like it would be the right length based on external observation, but turns out to be the wrong length when actually inserted into the vessel. Stents with post-insertion determination of length can be generally useful, but still have a number of limitations when used to treat cerebral aneurysms unless they also feature advanced approaches to creating variability in wall porosity. For the purposes of this classification system, we put stents with variable wall porosity in other categories. Accordingly, the main feature of stents in this present category is post-insertion determination of length.

Limitations of such stents for treating cerebral aneurysms include the following. If the walls are too porous, then they will not sufficiently occlude the aneurysm and may allow blood clots or embolic members to escape from the aneurysm. Since most stents in this category involve meshes or spirals, especially linked to the mechanism of post-insertion length determination, high porosity can be a side effect of lengthening. This may not be a problem when stents are used for angioplasty, but can be a problem when stents are used to treat aneurysms. On the other hand, if the walls are too impermeable, then they may block blood flow to nearby branching vessels. Although stents in this category allow users to adjust the length of a stent in situ, they do not enable adjustment, either pre-insertion or post-insertion, of wall porosity. They do not allow the user to create different wall areas with lower or higher porosity. This also limits their usefulness for stenting cerebral aneurysms.

Examples of prior art that appear to fit within this category include: U.S. Pat. No. 7,326,236 (Andreas et al., 2008, "Devices and Methods for Controlling and Indicating the Length of an Interventional Element"); U.S. Pat. No. 7,892,273 (George et al., 2011, "Custom Length Stent Apparatus"); and U.S. Pat. No. 7,959,662 (Erbel et al., 2011, "Endovascular Prosthesis"); as well as U.S. patent applications 20050055077 (Marco et al., 2005, "Very Low Profile Medical Device System Having an Adjustable Balloon"); 20050149159 (Andreas et al., 2005, "Devices and Methods for Controlling and Indicating the Length of an Interventional Element"); 20050209674 (Kutscher et al., 2005, "Balloon Assembly V"); and 20070150045 (Ferrera, 2007, "Methods and Apparatus for Treating Aneurysms and other Vascular Defects").

B2. Stents with In Situ (Post-Insertion, Pre-Expansion) Determination of Multiple Stent Delivery The previous category included stents wherein stent length can be adjusted in situ, after insertion of the stent into the blood vessel. A related concept is a device that allows the delivery of multiple stents, wherein the number of stents is determined in situ by the user. These two categories are related because, in some respects, they are alternative ways of varying the length of the vessel that is stented. Stents in the previous category let the user adjust the length of the vessel that is stented by varying the length of a single stent after insertion of the stent into the parent blood vessel. Stents in this present category let the user adjust the length of the vessel that is stented by deploying (a chain of) multiple stents. The pros and cons of both concepts are similar.

Giving a user the ability to select how many stents are deployed after the device has been inserted into the parent blood vessel is useful for reducing the variety of stents needed for inventory and for tailoring the length of the vessel treated in real-time based on observation of the device within the vessel. It can also save time when multiple stents are required. The user does not have to separately introduce multiple catheters for multiple stent deployments. Stents with post-insertion determination of multiple stent delivery can be useful, but have a number of limitations when used to treat cerebral aneurysms unless they also feature advanced approaches to creating variability in wall porosity. If the walls are too porous, then they will not sufficiently occlude the aneurysm. They may allow blood clots or embolic members to escape from the aneurysm. On the other hand, if the walls are too impermeable, then they may block blood flow to nearby branching vessels. Although stents in this category allow users to adjust the length of a vessel that is treated in situ, they do not enable adjustment, either pre-insertion or post-insertion, of wall porosity or determination of different wall areas with lower or higher porosity. This limits their usefulness for stenting cerebral aneurysms.

Examples of prior art that appear to fit within this category include: U.S. Pat. No. 5,755,781 (Jayaraman, 1998, "Embodiments of Multiple Interconnected Stents"); U.S. Pat. No. 6,258,117 (Camrud et al., 2001, "Multi-Section Stent"); U.S. Pat. No. 6,485,510 (Camrud et al., 2002, "Multi-Section Stent"); U.S. Pat. No. 7,137,993 (Acosta et al., 2006, "Apparatus and Methods for Delivery of Multiple Distributed Stents"); U.S. Pat. No. 7,147,655 (Chermoni, 2006, "Balloon Catheter for Multiple Adjustable Stent Deployment"); U.S. Pat. No. 7,294,146 (Chew et al., 2007, "Apparatus and Methods for Delivery of Variable Length Stents"); U.S. Pat. No. 7,905,913 (Chew et al., 2011, "Apparatus and Methods for Delivery of Multiple Distributed Stents"); U.S. Pat. No. 7,922,755 (Acosta et al., 2011, "Apparatus and Methods for Delivery of Multiple Distributed Stents"); U.S. Pat. No. 7,963,987 (Melsheimer et al., 2011, "Sequential Implant Delivery System"); U.S. Pat. No. 8,012,192 (Eidenschink et al., 2011, "Multi-Stent Delivery System"); U.S. Pat. No. 8,012,196 (Smith et al., 2011, "Flexible Segmented Stents"); U.S. Pat. No. 8,016,870 (Chew et al., 2011, "Apparatus and Methods for Delivery of Variable Length Stents"); and U.S. Pat. No. 8,016,871 (Chew et al., 2011, "Apparatus and Methods for Delivery of Multiple Distributed Stents"); as well as U.S. patent applications 20040215312 (Andreas, 2004, "Stent Delivery Apparatus and Method"); 20070088368 (Acosta et al., 2007, "Apparatus and Methods for Delivery of Multiple Distributed Stents"); 20100318173 (Kolandaivelu et al., 2010, "Endovascular Devices Catheter Platforms and Methods for Achieving Congruency in Sequentially Deployed Devices"); and 20110152996 (Acosta et al., 2011, "Apparatus and Methods for Delivery of Multiple Distributed Stents").

B3. Stents with In Situ (Post-Insertion, Pre-Expansion) Determination of Longitudinal Axis Curvature Included among the above stent categories was a category for stents with pre-insertion variation in stent flexibility. These are useful for navigation and deployment in tortuous vessels. This present category takes the concept of longitudinal flexibility and adaptability for curved vessels one step further. Stents in this category go beyond passive flexibility. These stents allow users to actively adjust the longitudinal axis curvature of a stent in situ. This degree of control allows greater customization to the curvature and configuration of a parent vessel. However, stents that have been placed into this category do not have advanced mechanisms for varying stent wall porosity, either pre or post insertion. Accordingly, they have limitations as a treatment for cerebral aneurysms. If the stent walls are too porous, then they will not sufficiently block blood flow to the aneurysm. If the stent walls are too impermeable, then they can block the entrances to nearby branching blood vessels. There is no mechanism in this category that allows the user to adjust the level of variability of stent wall porosity. Such stents appear to be uncommon.

Examples of prior art that appear to fit within this category include: U.S. Pat. No. 6,579,308 (Jansen et al., 2003, "Stent Devices with Detachable Distal or Proximal Wires"); U.S. Pat. No. 7,063,719 (Jansen et al., 2006, "Stent Devices with Detachable Distal or Proximal Wires"); U.S. Pat. No. 7,722,657 (Hartley, 2010, "Asymmetric Stent Graft Attachment"); and U.S. Pat. No. 7,998,189 (Kolbel et al., 2011, "Curvable Stent-Graft and Apparatus and Fitting Method"); as well as U.S. patent applications 20040073289 (Hartley, 2004, "Asymmetric Stent Graft Attachment"); and 20040249435 (Andreas et al., 2004, "Stent Deployment Systems and Methods").

B4. Stents with In Situ (Post-Insertion, Pre-Expansion) Determination of Longitudinal Taper (or Other Longitudinal Variation in Cross-Sectional Size or Shape)

This category includes stents with longitudinal variation in cross-sectional size or shape that can be adjusted in situ (after insertion of the stent into the parent blood vessel) but before stent expansion. Such stents have the advantages of stents with pre-insertion longitudinal variation in cross-sectional size or shape, supplemented with the ability to adjust this variation in situ. Since the stent can be customized in situ, this reduces the need for precise configuration of the stent to the shape and size of the vessel prior to insertion. It also reduces the need for precise longitudinal and rotational placement of the stent in the vessel. Since the user has the flexibility to change the longitudinal variation in situ, the stent need not be rotated in a particular direction. Despite the advantages of such an adjustable tapered stent, such stents do not offer adjustment of wall porosity. As such, they are not ideal for treating cerebral aneurysms. If the stent's walls are too porous, then they do not block blood flow into the aneurysm. If the stent's walls are too impermeable, then they block blood flow into nearby branching vessels. Such stents do not enable the user to create areas of differential wall porosity to resolve this dilemma. Stents in this category are uncommon in the prior art. Examples of prior art that appear to fit within this category are U.S. Pat. No. 6,497,722 (Von Oepen et al., 2002, "Methods and Apparatus for In-Vivo Tailored Stents Indicated for Use in Tortuous Anatomy") and U.S. patent application 20100114302 (Tzafriri et al., 2010, "Endovascular Devices with Axial Perturbations").

B5. Stents with In Situ (Post-Insertion, Pre-Expansion) Determination of Asymmetric Cross-Sectional Perimeter Stents in this category allow a user to determine the asymmetry of a stent's cross-sectional perimeter shape in situ (after insertion of the stent into the parent blood vessel) but before the stent's expansion. Such stents have the advantages of stents with pre-insertion determination of an asymmetric cross-sectional perimeter shape, supplemented by the advantage that this shape can be adjusted in situ. This reduces the need for precise configuration of the stent to the shape and size of the vessel outside the body. It also reduces the need for precise longitudinal and rotational placement of the stent in the vessel. Recalling our prior discussion of the difference between stent shape and stent porosity, it is important to note that such stents do not have adjustable porosity. Accordingly, if the stent's walls are too porous, then they will not block blood flow into the aneurysm. If the stent's walls are too impermeable, then they may block blood flow into nearby branching vessels. Such stents do not allow the user to create areas of differential wall porosity to resolve this dilemma. Stents in this category appear to be very uncommon in the prior art. One example of prior art that appears to fit within this category is U.S. patent application 20100114302 (Tzafriri et al., 2010, "Endovascular Devices with Axial Perturbations").

B6. Stents with In Situ (Post-Insertion, Pre-Expansion) Determination of Low or High Porosity (Ring) Segment Along Wall Stents in this category allow a user to create segments (thick "rings") of the stent wall with lower or higher porosity, in situ, after insertion of a stent into the parent blood vessel but before its expansion. Such stents have the advantages of stents with pre-insertion determination of segments of the stent wall with low or high porosity. They also have the additional advantage that this variation in porosity can be adjusted in situ. This reduces the need for precise configuration of the stent to the shape and size of the vessel and also reduces the need for precise longitudinal and rotational placement of the stent in the vessel. However, despite all these advantages, such stents are still limited by their inability to create differences in wall porosity around the perimeter of a stent cross section. Accordingly, these stents do not work well when the neck of an aneurysm is diametrically opposite the entrance to a branch vessel or is in a forked vessel. Stents in this category appear to be uncommon in the prior art. One example of prior art that appears to fit within this category is U.S. patent application 20070150045 (Ferrera, 2007, "Methods and Apparatus for Treating Aneurysms and other Vascular Defects").

C. Stents with In Situ (Post-Expansion) Determination of Configuration

This major category in the classification scheme includes stents whose configuration can be changed after the stent has been inserted and expanded within a blood vessel. As we discussed previously, there are some methods of stent configuration that only work after the stent has been expanded. For example, filling irregularities (or "gaps") between the expanded stent wall and the vessel wall only works after the stent has been expanded. There are also methods of stent configuration (in the previous major category) that do not work after stent expansion.

C1. Stents with In Situ (Post-Expansion) Determination of Low or High Porosity (Ring) Segment Along Wall Stents in this category can be adjusted in situ, after the stent has been inserted and also expanded within the blood vessel. Stents in this category enable a user, generally a physician, to create low or high porosity segments (thick "rings") along the length of the stent after it has been expanded. This capability is useful. The user does not have to precisely configure the stent to match the configuration of the parent vessel before it is inserted into the body. This configuration can be determined in situ. Also, the user does not have to precisely position the stent so that pre-determined features line up precisely with the aneurysm neck and any branching vessels. The user can adjust the configuration of low and high porosity segments to match vessel features, in real time, after the stent is positioned in the vessel.

There are a couple different technologies for making such post-expansion adjustments of wall porosity in the prior art. One technology for creating low or high porosity segments involves post-expansion activation of a surface coating on a selected area of the stent wall. This may be done by selectively exposing that area to a certain type of energy or to certain chemicals. Another technology for creating low porosity areas of the stent wall after expansion involves coating a selected area of the stent wall. This may be done by targeted release of chemicals onto that area of the stent wall. However, these technologies have limitations. It can be challenging to accurately target energy emissions or chemical coatings to a specific area of the stent wall inside a tiny, tortuous vessel with complex fluid dynamics. Also, there can be negative health effects from the process used to modify the stent wall. Energy emissions may harm surrounding brain tissue. Chemical coatings may disperse into the blood stream with negative systemic effects. Stents in this category also have other limitations for use to treat cerebral aneurysms. For example, they do not enable a user to create differential wall porosity around the perimeter of a stent cross section. According, they do not work in situations in which there is a branch vessel opposite the aneurysm neck. Finally, since the mechanism of action for stents in this category is after expansion of the stent, this category does not allow the user to concentrate wall mass (creating an area of low porosity) over the aneurysm neck by different expansion. Examples of prior art that appear to fit within this category are U.S. patent applications 20050283220 (Gobran et al., 2005, "Blood Flow Diverters for the Treatment of Intracranial Aneurysms") and 20070060994 (Gobran et al., 2007, "Blood Flow Diverters for the Treatment of Intracranial Aneurysms").

C2. Stents with In Situ (Post-Expansion) Determination of Low or High Porosity (Convex) Area on Wall Like stents in the previous category, stents in this category can be adjusted in situ after the stent has been both inserted and expanded within the blood vessel. Stents in this category allow greater flexibility in the shape of the low or high porosity wall areas that are created after stent expansion. Unlike stents in the previous category, low or high porosity areas in this category do not have to be segments ("rings") along the wall of the stent. In this category, these areas may be circles, saddle-shaped areas, or other (convex) shapes. Since the wall areas with differential porosity are determined in situ, the user does not have to precisely configure the stent to match the configuration of the parent vessel before it is inserted into the body. Also, the user does not have to precisely position the stent so that pre-determined features line up with the aneurysm neck and any branching vessels. The user can adjust the configuration of low and high porosity segments to match vessel features in real time after the stent is deployed in the vessel. As an advantage over stents in the previous category, stents in this category can also create differences in wall porosity in the perimeter of a given cross-section, allowing the stent to work even when the aneurysm neck is opposite the entrance to a branching vessel.

However, the mechanisms for post-expansion wall modification are like those for stents in the previous category and, thus, share their limitations. One mechanism for creating low or high porosity segments is post-expansion activation of a surface coating on a selected area of the stent wall by selectively exposing that area to targeted energy or chemicals. Another mechanism for creating low porosity areas of the stent wall after expansion involves coating a selected area of the stent wall by targeted release of chemicals near that area. It can be challenging to accurately target energy emissions or chemical coatings in a tiny tortuous vessel with complex fluid dynamics. There can also be negative side effects from the process used to modify the stent wall. For example, targeted energy emissions may harm surrounding brain tissue. Chemical coatings may release chemicals into the blood stream that have negative health effects. Finally, since the mechanism of action for stents in this category is after expansion of the stent, this category does not allow the user to concentrate wall mass (creating an area of low porosity) over the aneurysm neck by different expansion.

Examples of prior art that appear to fit within this category include: U.S. Pat. No. 5,951,599 (McCrory, 1999, "Occlusion System for Endovascular Treatment of an Aneurysm"); U.S. Pat. No. 6,673,385 (Ding et al., 2004, "Methods for Polymeric Coatings Stents"); U.S. Pat. No. 7,147,659 (Jones, 2006, "Expandable Stent Having a Dissolvable Portion"); U.S. Pat. No. 7,156,871 (Jones et al., 2007, "Expandable Stent Having a Stabilized Portion"); U.S. Pat. No. 7,572,288 (Cox, 2009, "Aneurysm Treatment Device and Method of Use"); and U.S. Pat. No. 7,611,530 (Pomeranz et al., 2009, "Expandable Stent Having Removable Slat Members"); as well as U.S. patent applications 20060095111 (Jones et al., 2006, "Expandable Stent Having a Stabilized Portion"); 20070067015 (Jones et al., 2007, "Expandable Stent Having a Stabilized Portion"); and 20100131002 (Connor et al., 2010, "Stent with a Net Layer to Embolize an Aneurysm").

D. Other Prior Art that is Potentially Relevant

Art in this fourth major category appears to be generally relevant to this disclosure, but does not neatly fit within one of the above three major categories. It includes general use of Micro ElectroMechancial Systems (MEMS), shape memory materials, and complex (e.g. multi-chambered) balloon configurations.

D1. Stents with Micro ElectroMechancial Systems (MEMS)

This category includes prior art with application of Micro ElectroMechanical Systems (MEMS) to stents that did not fit within one of the above three categories. Commercial application of MEMS to stents will probably take a number of years and will depend on further technological development. With the limitations of current technology and manufacturing methods, there are a number of challenges to application of MEMS to stents including: manufacturing complexity and cost, challenges with respect to size and inflexibility for use in tortuous vessels, and energy source and control mechanism for MEMS activation. Nonetheless, the concept has potential and there is at least some prior art that generally discloses application of MEMS technology to stent expansion. This art does not appear to disclose in situ control of differential wall porosity, but it is potentially relevant due to its general discussion of using MEMS technology for stent expansion. Examples of prior art that appear to fit within this category are U.S. Pat. No. 7,141,063 (White et al., 2006, "Stent with Micro-Latching Hinge Joints") and U.S. Pat. No. 7,235,098 (Palmaz, 2007, "Medical Devices Having MEMS Functionality and Methods of Making Same").

D2. Stents with Shape Memory Materials

This category includes prior art with general application of shape memory materials to stents that does not fit within one of the above three categories. This art does not appear to disclose in situ control of differential wall porosity, but it is potentially relevant due to its general discussion of using shape memory technology for stent expansion. Examples of prior art that appear to fit within this category include: U.S. Pat. No. 5,603,722 (Phan et al., 1997, "Intravascular Stent"); U.S. Pat. No. 5,964,744 (Balbierz et al., 1999, "Polymeric Medical Device Systems Having Shape Memory"); U.S. Pat. No. 6,569,193 (Cox et al., 2003, "Tapered Self-Expanding Stent"); U.S. Pat. No. 6,579,305 (Lashinski, 2003, "Method and Apparatus for Delivery Deployment and Retrieval of a Stent Comprising Shape-Memory Material"); U.S. Pat. No. 6,676,692 (Rabkin et al., 2004, "Apparatus for Delivering/Repositioning and/or Retrieving Self-Expanding Stents"); U.S. Pat. No. 6,837,901 (Rabkin et al., 2005, "Methods for Delivering/Repositioning and/or Retrieving Self-Expanding Stents"); U.S. Pat. No. 7,037,327 (Salmon et al., 2006, "Stent with Self-Expanding End Sections"); and U.S. Pat. No. 8,012,197 (Bashiri et al., 2011, "Hybrid Balloon Expandable/Self-Expanding Stent"); as well as U.S. patent application 20110137405 (Wilson et al., 201, "Stent with Expandable Foam").

D3. Complex Balloon Configurations

This category includes prior art with complex balloon configurations such as multi-chambered balloons or sequential inflation of multiple balloons. Some examples of this art relate to the use of complex balloon configurations to expanding stents. Other examples do not explicitly relate to stents but are nonetheless potentially relevant because of their innovative disclosure of complex balloons that could be used for stent expansion. This art does not appear to disclose in situ control of differential wall porosity, but it is potentially relevant due to its general discussion of using complex balloon configurations.

Examples of prior art that appear to fit within this category include: U.S. Pat. No. 5,226,889 (Sheiban, 1993, "Double Balloon Catheter for Stent Implantation"); U.S. Pat. No. 5,304,132 (Jang, 1994, "Limacon Geometry Balloon Angioplasty Catheter Systems and Method of Making Same"); U.S. Pat. No. 5,308,323 (Sogawa et al., 1994, "Multiple Compartment Balloon Catheter"); U.S. Pat. No. 5,536,252 (Imran et al., 1996, "Angioplasty Catheter with Multiple Coaxial Balloons"); U.S. Pat. No. 5,545,209 (Roberts et al., 1996, "Controlled Deployment of a Medical Device"); U.S. Pat. No. 5,704,913 (Abele et al., 1998, "Dilation Catheter and Method of Treatment Therewith"); U.S. Pat. No. 5,833,657 (Reinhardt et al., 1998, "Single-Walled Balloon Catheter with Non-Linear Compliance Characteristic"); U.S. Pat. No. 5,908,448 (Roberts et al., 1999, "Controlled Deployment of a Medical Device"); U.S. Pat. No. 6,123,712 (Di Caprio et al., 2000, "Balloon Catheter with Stent Securement Means"); U.S. Pat. No. 6,136,011 (Stambaugh, 2000, "Stent Delivery System and Method of Use"); U.S. Pat. No. 6,296,660 (Roberts et al., 2001, "Controlled Deployment of a Medical Device"); U.S. Pat. No. 6,419,685 (Di Caprio et al., 2002, "Balloon Catheter with Stent Securement Means"); U.S. Pat. No. 6,471,672 (Brown et al., 2002, "Selective High Pressure Dilation Balloon"); U.S. Pat. No. 6,506,201 (Di Caprio et al., 2003, "Balloon Catheter with Stent Securement Means"); U.S. Pat. No. 6,605,056 (Eidenschink et al., 2003, "Conformable Balloon"); U.S. Pat. No. 6,872,223 (Roberts et al., 2005, "Controlled Deployment of a Medical Device"); U.S. Pat. No. 7,052,510 (Richter, 2006, "Two Balloon Staged Stent Expansion"); U.S. Pat. No. 7,081,129 (Chobotov, 2006, "Endovascular Graft"); U.S. Pat. No. 7,147,660 (Chobotov et al., 2006, "Advanced Endovascular Graft"); U.S. Pat. No. 7,147,661 (Chobotov et al., 2006, "Radially Expandable Stent"); U.S. Pat. No. 7,615,071 (Chobotov, 2009, "Endovascular Graft"); U.S. Pat. No. 7,651,525 (Dolan, 2010, "Intraluminal Stent Assembly and Method of Deploying the Same"); U.S. Pat.

No. 7,695,488 (Berenstein et al., 2010, "Expandable Body Cavity Liner Device"); U.S. Pat. No. 7,776,079 (Gumm, 2010, "Conical Balloon for Deployment into Side Branch"); and U.S. Pat. No. 7,942,847 (Stupecky et al., 2011, "Multi-Layer Balloons for Medical Applications and Methods for Manufacturing the Same").

Examples that appear to fit within this category also include: U.S. patent applications 20020045914 (Roberts et al., 2002, "Controlled Deployment of a Medical Device"); 20030014007 (Eidenschink et al., 2003, "Conformable Balloon"); 20050209674 (Kutscher et al., 2005, "Balloon Assembly (V)"); 20070100301 (Gumm, 2007, "Conical Balloon for Deployment into Side Branch"); 20080097374 (Korlesk et al., 2008, "Inflatable Shaped Balloons"); 20100094247 (Kaluski, 2010, "Bifurcated Balloon & Stent Delivery System"); 20100305681 (Gumm, 2010, "Conical Balloon for Deployment into Side Branch"); and 20110238105 (Gelbart et al., 2011, "Vivo Inflatable Structures for Example to Expand Stents").

D4. Other Potentially-Relevant Prior Art

This last category is a miscellaneous category that includes prior art related to aneurysm treatment and stents that does not fit within any of the above categories and does not appear to disclose in situ control of differential wall porosity, but it is potentially relevant nonetheless. Examples of prior art that appear to fit within this category include: U.S. Pat. No. 5,258,042 (Mehta, 1993, "Intravascular Hydrogel Implant"); U.S. Pat. No. 5,411,549 (Peters, 1995, "Selectively Expandable/Retractable and Removable Stent"); U.S. Pat. No. 5,441,515 (Khosravi et al., 1995, "Ratcheting Stent"); U.S. Pat. No. 5,443,495 (Buscemi et al., 1995, "Polymerization Angioplasty Balloon Implant Device"); U.S. Pat. No. 5,464,449 (Ryan et al., 1995, "Internal Graft Prosthesis and Delivery System"); U.S. Pat. No. 5,749,894 (Engelson, 1998, "Aneurysm Closure Method"); U.S. Pat. No. 5,843,158 (Lenker et al., 1998, "Limited Expansion Endoluminal Prostheses and Methods for Their Use"); U.S. Pat. No. 5,873,907 (Frantzen, 1999, "Electrolytic Stent Delivery System and Methods of Use"); U.S. Pat. No. 5,911,754 (Kanesaka et al., 1999, "Flexible Stent with Effective Strut and Connector Patterns"); U.S. Pat. No. 5,980,514 (Kupiecki et al., 1999, "Aneurysm Closure Device Assembly"); U.S. Pat. No. 6,004,261 (Sinofsky et al., 1999, "Formed-In-Place Endovascular Stent and Delivery System"); U.S. Pat. No. 6,063,111 (Hieshima et al., 2000, "Stent Aneurysm Treatment System and Method"); U.S. Pat. No. 6,086,610 (Duerig et al., 2000, "Composite Self Expanding Stent Device Having a Restraining Element"); and U.S. Pat. No. 6,093,199 (Brown et al., 2000, "Intra-Luminal Device for Treatment of Body Cavities and Lumens and Method of Use").

Additional examples include: U.S. Pat. No. 6,096,034 (Kupiecki et al., 2000, "Aneurysm Closure Device Assembly"); U.S. Pat. No. 6,149,681 (Houser et al., 2000, "Radially Expanding Prostheses and Systems for Their Deployment"); U.S. Pat. No. 6,168,615 (Ken et al., 2001, "Method and Apparatus for Occlusion and Reinforcement of Aneurysms"); U.S. Pat. No. 6,168,622 (Mazzocchi, 2001, "Method and Apparatus for Occluding Aneurysms"); U.S. Pat. No. 6,273,911 (Cox et al., 2001, "Variable Strength Stent"); U.S. Pat. No. 6,312,421 (Boock, 2001, "Aneurysm Embolization Material and Device"); U.S. Pat. No. 6,315,791 (Gingras et al., 2001, "Self-Expanding Prosthesis"); U.S. Pat. No. 6,331,191 (Chobotov, 2001, "Layered Endovascular Graft"); U.S. Pat. No. 6,340,366 (Wijay, 2002, "Stent with Nested or Overlapping Rings"); U.S. Pat. No. 6,344,041 (Kupiecki et al., 2002, "Aneurysm Closure Device Assembly"); U.S. Pat. No. 6,409,749 (Maynard, 2002, "Aneurism Patch Including Distributed Activator for a Two-Dimensional Shape Memory Alloy"); U.S. Pat. No. 6,416,543 (Hilaire et al., 2002, "Expandable Stent with Variable Thickness"); U.S. Pat. No. 6,432,128 (Wallace et al., 2002, "Intracranial Stent and Method of Use"); U.S. Pat. No. 6,475,233 (Trozera, 200, "Stent Having Tapered Struts"); U.S. Pat. No. 6,511,505 (Cox et al., 2003, "Variable Strength Stent"); U.S. Pat. No. 6,520,985 (Burpee et al., 2003, "Stent with Reduced Shortening"); U.S. Pat. No. 6,520,987 (Plante, 2003, "Expandable Intravascular Stent"); U.S. Pat. No. 6,607,539 (Hayashi et al., 2003, "Electric Endovascular Implant Deployment System"); and U.S. Pat. No. 6,645,237 (Klumb et al., 2003, "Expandable Coiled Endoluminal Prosthesis").

Further examples that appear to fit within this category include: U.S. Pat. No. 6,660,032 (Klumb et al., 200, "Expandable Coil Endoluminal Prosthesis"); U.S. Pat. No. 6,663,607 (Slaikeu et al., 2003, "Bioactive Aneurysm Closure Device Assembly and Kit"); U.S. Pat. No. 6,669,719 (Wallace et al., 2003, "Intracranial Stent and Method of Use"); U.S. Pat. No. 6,673,103 (Golds et al., 2004, "Mesh and Stent for Increased Flexibility"); U.S. Pat. No. 6,716,238 (Elliott, 2004, "Stent with Detachable Tethers and Method of Using Same"); U.S. Pat. No. 6,719,783 (Lentz et al., 2004, "PTFE Vascular Graft and Method of Manufacture"); U.S. Pat. No. 6,780,196 (Chin et al., 2004, "Removable Occlusion System for Aneurysm Neck"); U.S. Pat. No. 6,786,920 (Shannon et al., 2004, "Stented Radially Expandable Tubular PTFE Grafts"); U.S. Pat. No. 6,790,225 (Shannon et al., 2004, "Stented Radially Expandable Tubular PTFE Grafts"); U.S. Pat. No. 6,811,560 (Jones et al., 2004, "Stent Aneurysm Embolization Method and Device"); U.S. Pat. No. 6,833,003 (Jones et al., 2004, "Expandable Stent and Delivery System"); U.S. Pat. No. 7,083,640 (Lombardi et al., 2006, "Covered Stent with Encapsulated Ends"); U.S. Pat. No. 7,169,172 (Levine et al., 2007, "Method and Apparatus for Caged Stent Delivery"); U.S. Pat. No. 7,195,648 (Jones et al., 2007, "Intravascular Stent Device"); U.S. Pat. No. 7,323,005 (Wallace et al., 2008, "Intracranial Stent and Method of Use"); U.S. Pat. No. 7,384,426 (Wallace et al., 2008, "Intracranial Stent and Method of Use"); U.S. Pat. No. 7,563,270 (Gumm, 2009, "Rotating Stent Delivery System for Side Branch Access and Protection and Method of Using Same"); U.S. Pat. No. 7,608,088 (Jones et al., 2009, "Stent Aneurysm Embolization Device"); U.S. Pat. No. 7,666,220 (Evans et al., 2010, "System and Methods for Endovascular Aneurysm Treatment"); U.S. Pat. No. 7,862,602 (Licata et al., 2011, "Indirect-Release Electrolytic Implant Delivery Systems"); U.S. Pat. No. 7,914,574 (Schmid et al., 2011, "Axially Nested Slide and Lock Expandable Device"); U.S. Pat. No. 7,914,639 (Layne et al., 2011, "Partial Encapsulation of Stents"); U.S. Pat. No. 7,947,071 (Schmid et al., 2011, "Expandable Slide and Lock Stent"); U.S. Pat. No. 7,988,719 (Alt et al., 2011, "Vascular Stent with Composite Structure for Magnetic Resonance Imaging Capabilities"); U.S. Pat. No. 7,988,721 (Morris et al., 2011, "Axially-Radially Nested Expandable Device"); U.S. Pat. No. 7,993,385 (Levine et al., 2011, "Method and Apparatus for Caged Stent Delivery"); U.S. Pat. No. 8,007,527 (Thompson, 2011, "Stent with Dual Support Structure"); U.S. Pat. No. 8,016,853 (Griffen et al., 2011, "Sacrificial Anode Stent System"); U.S. Pat. No. 8,016,876 (Gregorich et al., 2011, "Stent Configurations"); U.S. Pat. No. 8,021,416 (Abrams, 2011, "Methods for Delivering a Prosthesis to a Site in a Body"); and RE42,758 (Ken et al., 2011, "Expandable Curvilinear Strut Arrangement for Deployment with a Catheter to Repair an Aneurysm").

Examples of U.S. patent applications that also appear to fit within this category include: 20030065375 (Eskuri, 2003, "Nested Stent Apparatus"); 20040044391 (Porter, 2004, "Device for Closure of a Vascular Defect and Method of Treating the Same"); 20040186551 (Kao et al., 2004, "Multiple Independent Nested Stent Structures and Methods for Their Preparation and Deployment"); 20050107863 (Brown, 2005, "Micro Structure Stent Configurations"); 20050177186 (Cully et al., 2005, "Endoluminal Devices"); 20050192620 (Cully et al., 2005, "Methods of Manufacture and Use of Endoluminal Devices"); 20050267570 (Shadduck, 2005, "Endovascular Occlusion Devices and Methods Of Use"); 20060206196 (Porter, 2006, "Device for Closure of a Vascular Defect and Method for Treating the Same"); 20070207186 (Scanlon et al., 2007, "Tear and Abrasion Resistant Expanded Material and Reinforcement"); 20070276469 (Tenne, 2007, "Occlusion Device Combination of Stent and Mesh with Diamond-Shaped Porosity"); 20070276470 (Tenne, 2007, "Occlusion Device Combination of Stent And Mesh with Diamond-Shaped Porosity"); 20080097495 (Feller et al., 2008, "Thin Film Metallic Device for Plugging Aneurysms or Vessels"); and 20080195137 (Alleyne et al., 2008, "Devices and Methods for Aneurysm Treatment").

These examples further include: 20090082846 (Chobotov, 2009, "Asymmetric Stent Apparatus and Method"); 20090125053 (Ferrera et al., 2009, "Aneurysm Neck Bridging Processes with Revascularization Systems Methods and Products Thereby"); 20090275974 (Marchand et al., 2009, "Filamentary Devices for Treatment of Vascular Defects"); 20090318949 (Ganpath et al., 2009, "Sealing Apparatus and Methods of Use"); 20100069948 (Vezneedaroglu et al., 2010, "Self-Expandable Aneurysm Filling Device System and Method of Placement"); 20100222804 (Murphy et al., 2010, "Detachable Aneurysm Neck Bridge"); 20110046658 (Connor et al., 2011, "Aneurysm Occlusion Device"); 20110144669 (Becking et al., 2011, "Aneurysm Cover Device for Embolic Delivery and Retention"); 20110152993 (Marchand et al., 2011, "Multiple Layer Filamentary Devices or Treatment of Vascular Defects"); 20110184452 (Huynh et al., 2011, "Vascular Remodeling Device"); 20110184453 (Levy et al., 2011, "Vascular Remodeling Device"); 20110190867 (Vonderwalde et al., 2011, "Directional Expansion of Intraluminal Devices"); and 20110230951 (Cully et al., 2011, "Device for Rapid Repair of Body Conduits").

SUMMARY OF THIS INVENTION

This invention comprises a method and a device that give a physician in situ (post-insertion, pre-expansion) control to create differences in wall porosity between different areas of a stent wall. This enables a physician to customize the stent within a blood vessel to selectively block blood flow to an aneurysm with a low-porosity area of the stent wall, but also allow blood flow to nearby branching vessels through one or more high-porosity areas of the stent wall. The method comprises inserting a stent into a blood vessel and, in situ, expanding the stent in a non-uniform manner, thereby causing one or more areas of the stent wall to have a lower post-expansion porosity than the rest of the stent wall. The related device comprises a stent which enables such non-uniform expansion in situ.

Post-expansion differences in stent wall porosity may be cross-sectional perimeter differences, longitudinal differences, or both. A cross-sectional perimeter difference in wall porosity exists when the stent may be viewed as having at least one lateral cross-section and there are differences in porosity between two or more wall areas at different locations around the cross-sectional perimeter of this lateral cross section. A longitudinal difference in wall porosity exists when the stent may be viewed as having a longitudinal axis (which may be straight or curved) and there are differences in porosity between two or more wall areas at different locations along this longitudinal axis.

In different embodiments of this invention, a physician may selectively determine one or more post-expansion low-porosity wall areas after insertion of the stent and before expansion of the stent using a means selected from the group consisting of: (a) detaching, removing, or stretching one or more expansion-resisting members among a plurality of expansion-resisting members, wherein these expansion-resisting members selectively restrict expansion of different areas of the stent wall, prior to expansion of the stent; (b) inflating one or more inflatable members among a plurality of inflatable members, or a plurality of chambers in a single inflatable member, wherein these inflatable members or chambers selectively expand different areas, respectively, of the stent wall; (c) activating one or more Micro-Electro-Mechanical Systems (MEMS) among a plurality of MEMS, wherein these MEMS selectively move different areas, respectively, of the stent wall; and (d) applying energy to, one or more shape-memory members among a plurality of shape-memory members, wherein these shape-memory members selectively move different areas, respectively, of the stent wall.

This invention has several advantages over options that are currently available to physicians for treating cerebral aneurysms—including surgical clipping, coiling, and stenting (using stents available in the prior art). This invention avoids the health risks of invasive surgery, addresses hemodynamic problems in the parent vessel of an aneurysm, and enables a physician to tailor in situ cross-sectional or longitudinal differences in stent wall porosity to the configuration of the vessel wherein it is deployed (using non-uniform stent expansion to create post-expansion differences in stent wall porosity). With this invention, physicians can selectively block blood flow into an aneurysm while maintaining blood flow into nearby branching vessels, even in tortuous and complex vessel configurations.

INTRODUCTION TO THE FIGURES

FIGS. 1 through 30 show multiple examples of ways in which this invention may be embodied, but these examples do not limit the full generalizability of the claims.

FIG. 1 shows a stent as one embodiment of this invention, after it has been inserted into a blood vessel with a wide-neck aneurysm but before in situ selective removal of some semi-circular members that resist cross-sectional expansion of the stent.

FIG. 2 shows this same stent after in situ selective removal of some of the expansion-resisting members, but before stent expansion.

FIG. 3 shows this same stent after non-uniform expansion that creates a low-porosity upper wall area covering the aneurysm and a high-porosity lower wall area covering branching vessels.

FIG. 4 shows a stent as one embodiment of this invention, after it has been inserted into a blood vessel with a wide-neck aneurysm but before in situ selective removal of some of the longitudinal band members that resist longitudinal expansion of the stent.

FIG. 5 shows this same stent after in situ selective removal of some of the expansion-resisting members, but before stent expansion.

FIG. 6 shows this same stent after non-uniform expansion that creates a low-porosity central segment covering the aneurysm and two high-porosity end segments covering branching vessels.

FIG. 7 shows two stents after insertion into a blood vessel juncture with a wide-neck aneurysm at the juncture, before in situ selective removal of some of the cross-sectional members that resist cross-sectional expansion of the stents.

FIG. 8 shows these same stents after in situ selective removal of some of the expansion-resisting members, but before stent expansion.

FIG. 9 shows these two stents after non-uniform expansion that creates low-porosity wall areas occluding the aneurysm neck and high-porosity wall areas allowing blood flow through vessel branches.

FIG. 10 shows a stent with many small-scale cross-sectional expansion-resisting members incorporated into the mesh of the stent wall, prior to any in situ adjustment and expansion.

FIG. 11 shows this stent after in situ selective removal of some of the expansion-resisting members, but before stent expansion.

FIG. 12 shows this stent after non-uniform expansion that creates an upper low-porosity wall area covering an aneurysm neck and a lower high-porosity wall area over the entrance to a branching vessel.

FIGS. 13-15 show how this invention can enable a user to adjust, in situ, the arcuate portion of a cross-sectional perimeter of the stent wall that will become low-porosity during expansion of the stent.

FIG. 13 shows a stent that has been non-uniformly expanded within a vessel with an aneurysm whose neck spans approximately 180 degrees of the parent vessel wall.

FIG. 14 shows a stent that has been non-uniformly expanded within a vessel with an aneurysm whose neck spans approximately 90 degrees of the parent vessel wall.

FIG. 15 shows a stent that has been non-uniformly expanded within a vessel with an aneurysm whose neck spans approximately 45 degrees of the parent vessel wall.

FIG. 16 shows a stent with many small-scale longitudinal expansion-resisting members incorporated into the mesh of the stent wall, prior to any in situ adjustment and expansion.

FIG. 17 shows this stent in situ selective removal of some of the longitudinal expansion-resisting members, but before stent expansion.

FIG. 18 shows this stent after non-uniform expansion that creates a left-side low-porosity wall area and a right-side high-porosity wall area.

FIG. 19 shows a tubular stent, pre-adjustment and pre-expansion, with a closed-cell mesh design, wherein each cell includes intra-cell cross-sectionally expandable members, intra-cell cross-sectionally expansion-resisting members, intra-cell longitudinal expandable members, and intra-cell longitudinal expansion-resisting members.

FIG. 20 shows this same stent after the in situ selective removal of some of the intra-cell cross-sectionally expansion-resisting members and subsequent non-uniform stent expansion.

FIG. 21 shows the same stent as in FIG. 19, in order to provide same-page comparison with FIG. 22.

FIG. 22 shows this stent after the in situ selective removal of some of the intra-cell longitudinal expansion-resisting members and subsequent non-uniform stent expansion.

FIG. 23 shows two parallel longitudinal inflatable members inside a mesh stent, prior to expansion.

FIG. 24 shows this same stent after in situ differential inflation of the members and non-uniform cross-sectional expansion of the stent.

FIG. 25 shows a longitudinal series of two inflatable members inside a mesh stent, prior to expansion.

FIG. 26 shows this same stent after in situ differential inflation of the members and non-uniform longitudinal expansion of the stent.

FIG. 27 shows a lateral cross-sectional view of two inflatable members inside a tubular mesh, before expansion.

FIG. 28 shows the same view after differential inflation and non-uniform expansion to create differential stent wall porosity.

FIG. 29 shows a lateral cross-sectional view of six inflatable members, distributed in a radially-symmetric manner, within a tubular mesh, before expansion.

FIG. 30 shows the same configuration as FIG. 29, but after differential inflation and non-uniform expansion to create differential stent wall porosity.

DETAILED DESCRIPTION OF THE FIGURES

FIGS. 1-30 show several examples of how this invention may be embodied. However, these figures are only examples. These figures do not limit the full generalizability of the claims.

Figure 1:
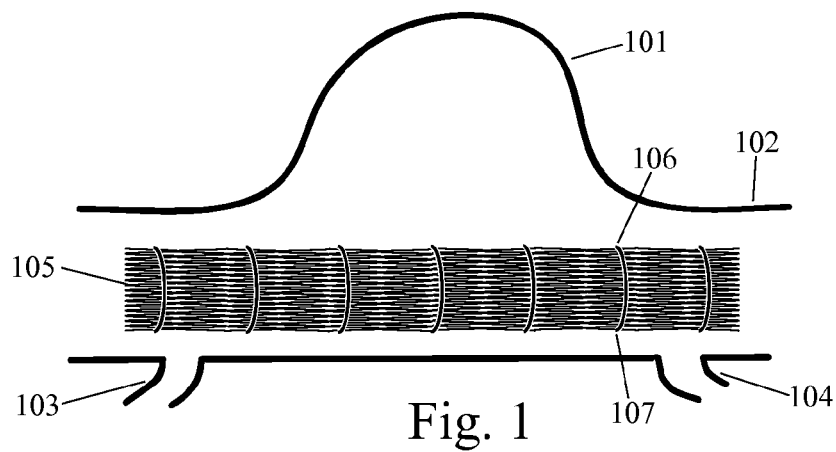
Figure 2:
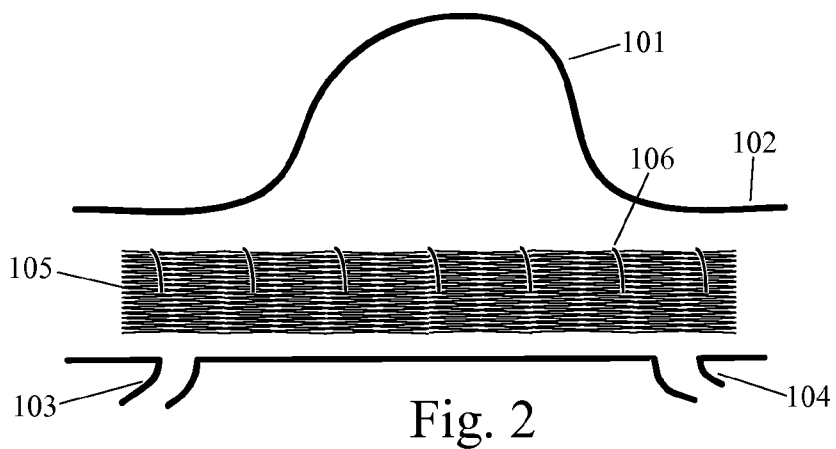
Figure 3:
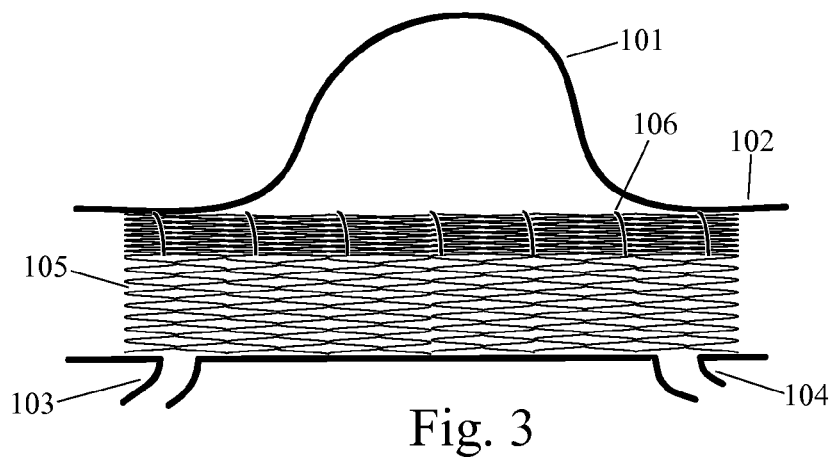

FIGS. 1-3 show an example of how this invention may be embodied to occlude a cerebral aneurysm, while still allowing continued blood flow to nearby branching blood vessels. In this example, a user creates a low-porosity area of the stent wall in situ, after insertion of the stent into the blood vessel. This low-porosity wall area spans the upper cross-sectional portion of a generally-tubular stent that is deployed in the parent vessel of the aneurysm. This low-porosity area of the stent wall substantially covers the aneurysm neck, thereby blocking blood flow into the aneurysm. The remaining high-porosity area of the stent wall provides support for the low-porosity area, without blocking blood flow to vessels that branch out from the opposite side of the parent vessel.

FIG. 1 shows a longitudinal cross-sectional view of a wide-neck aneurysm 101 comprising an outward bulge in the wall of parent vessel 102. FIG. 1 also shows branching blood vessels 103 and 104 whose entrances branch off from parent vessel 102 on the side of the vessel that is opposite from the aneurysm neck. In this example, stent 105 is an expandable tubular mesh scaffold that has been inserted longitudinally into parent vessel 102 such that it longitudinally spans the neck of aneurysm 101. FIG. 1 shows stent 105 after it has been inserted into parent vessel 102, but before it has been expanded. There are several methods disclosed in the prior art for inserting a stent into a blood vessel and the precise means by which insertion occurred is not central to this invention. There are also several methods disclosed in the prior art for expanding a stent within a blood vessel. In an example, the stent may be self-expanding. In another example, the stent may be expanded by inflation of a balloon inside it. The primary focus of this invention is on selectively removing constraints on expansion to cause non-uniform expansion, not the source of the expanding force. In various examples, the expandable mesh scaffold may be made from one or more of the following materials:

stainless steel, a nickel-titanium alloy, cobalt chromium or a cobalt-chromium alloy, titanium or a titanium alloy, tantalum or a tantalum allow, or polymeric-based resin or another polymer.

FIG. 1 also shows semi-circular ring section members, including 106 and 107, that each span half of the circular perimeter of one of the cross-sections of stent 105. In this example, the ring section members are semi-circular and each span half of the circular perimeter ("ring" or "hoop") of each cross-section of the stent. There is one semi-circular ring section member on the top portion of a cross-section and one semi-circular ring section member on the bottom portion of the cross-section. In other examples, there may be a larger number of smaller arcuate ring section members that combine to span the circular perimeter of cross-sections. For example, there may be four ring section members, each spanning 90-degrees of a circle, in each cross-section, or six ring section members, each spanning 60-degrees of a circle, in each cross-section. The larger the number of ring section members per cross-section, the greater the degree of accuracy for the user in controlling the cross-sectional non-uniform expansion of the stent. In the extreme, the stent may have a closed-cell design and each cell may have a removable member than resists cross-sectional expansion. In this example, these ring section members form seven rings (or "hoops") that circle the stent cross-sectionally and constrain its cross-sectional expansion. In other examples, there may be a lesser or greater number of rings circling the stent.

The main body of stent 105 is made from an expandable mesh. In an example, this mesh may be configured to allow expansion but not contraction. However, the ring section members, including 106 and 107, are configured to resist expansion. For example, they may span a portion of the circular perimeter of the cross-sections in flexible, but non-stretching, strands that are connected at one or more points to the main body of the stent. In this example, the ring section members, including 106 and 107, are attached to stent 105 so as to constrain its expansion, but these ring section members can be selectively removed from the stent.

The rings collectively formed by the ring section members constrain the radial expansion of stent 105. Removal of all of the ring sections would allow the stent to expand uniformly. Selective removal of only some of the ring sections in a cross section causes non-uniform expansion of the cross section. For example, removal of all the lower semi-circular ring members causes non-uniform expansion in which the lower portion of the stent to expands more than the upper portion of the stent. As another example, removal of all the upper semi-circular ring members would cause non-uniform expansion in which the upper portion of the stent would expand more than the lower portion of the stent. Non-uniform expansion results in post-expansion differences in wall porosity among different areas of the stent wall. Areas that expand more tend to be less porous. Areas that expand less tend to be more porous. In this manner, non-uniform stent expansion can be used to create, in situ, differential post-expansion wall porosity.

FIG. 1 shows that stent 105 will cover more than just the aneurysm neck when it is expanded. Stent 105 will also cover the entrances to branching vessels 103 and 104. This could cause problems. If one were to use a stent with a uniformly non-porous (impermeable to blood) wall, then such a stent would desirably block blood flow to the aneurysm, but it would also undesirably block blood flow to branching vessels 103 and 104. Lack of blood blow through vessels 103 and 104 would harm brain tissue that depends on those vessels. Accordingly, uniform stent wall porosity is undesirable. Differential post-expansion stent wall porosity is desirable. One would like a stent with low wall porosity over the aneurysm neck and high wall porosity over the entrances to the branching vessels. Ideally, one would like to give users the ability to create such differential porosity, in situ, based on the actual placement of the stent within the parent vessel. This invention provides users with such ability.

FIG. 2 shows the same stent that was introduced in FIG. 1, but after the semi-circular ring section members (including 107) on the lower side of the stent (opposite the aneurysm neck) have been selectively removed by the user. In this example, the user is a physician who is deploying the stent. The ring section members are removed in situ, after insertion of the stent into the parent vessel. In this example, the ring section members are removed in a similar manner from each of the stent cross-sections, causing longitudinal uniformity of the cross-sectional expansion. In another example, the ring sections may be removed in different manners from different stent cross-sections, causing longitudinal differences in cross-sectional expansion. As an example of the usefulness of the latter, a stent with a tapered post-expansion shape could be formed, in situ, to conform to the shape of a tapered parent vessel.

In this example, some of the ring section members are selectively removed by melting them with selective application of an electric current. For example, there may be separate circuits of electrical conductivity within the stent wall which connect to different ring section members or to different sets of ring section members. The user may remotely activate wires leading to some of these electrical circuits to selectively (and accurately) melt only certain ring section members in order to create the desired pattern of non-uniform stent expansion. Several methods of melting portions of an implantable device in situ by applying electric current are known in the prior art. In other examples, some of the ring section members may be removed by melting using thermal energy, by dissolving ring section members using a chemical process, or by manually removing them by sequential grasping and pulling. It is important to note that this selective removal of ring section members is radially asymmetric with respect to cross-sections of stent 105. Ring sections on the aneurysm side of stent 105, including 106, remain attached to stent 105.

FIG. 3 shows this same stent after the stent has been expanded. Since the expansion-resisting ring section members have been selectively removed, as shown in FIG. 2, the stent has expanded non-uniformly. The upper portion of stent 105, covering the aneurysm neck, has been constrained by ring section members, including 106, and has not expanded. Its curvature has changed to a wider arc in response to the expansive force of the lower portion of the stent, but its porosity remains the same as it was before expansion of the stent. Since the pre-expansion porosity of a mesh structure is lower than the post-expansion porosity of this mesh structure, the upper portion has a lower porosity and the lower portion has a higher porosity. In this manner, non-uniform mesh expansion is able to selectively concentrate the mass of the mesh over the aneurysm neck so as to create a low-porosity area over the aneurysm neck. Having a low-porosity area that is an integrated part of a tubular stent in the parent vessel has advantages over stand-alone "aneurysm neck patches" in the prior art. First, because it is created from a mesh structure, it can be flexible enough to navigate through tortuous vessels. Second, because it is an integral part of an entire tubular structure, it is easier to place and less likely to migrate than a stand-alone patch with a non-circumferential support structure.

The lower portion of stent 105, covering the entrances to branching vessels 103 and 104, was not constrained during expansion by ring section members because the lower ring section members, including 107, had been removed. As a result of this non-uniform expansion, which is determined by the user in situ by selective removal of ring section members, the expanded stent has an upper area with lower porosity that covers the aneurysm neck and a lower area with higher porosity that covers the entrances to the branching vessels. Proper blood flow to the branching vessels is maintained.

With respect to an innovative method, FIGS. 1-3 show an example of a method of creating differences in porosity between different areas of a stent wall comprising: inserting the stent into a blood vessel; and expanding the stent with non-uniform stent expansion, wherein non-uniform stent expansion is expansion in which different areas of the stent wall move different distances during stent expansion, wherein this non-uniform stent expansion causes one or more areas of the stent wall to have a lower porosity than the rest of the stent wall after stent expansion, and wherein the locations of these one or more areas, relative to the rest of the stent wall, can be determined or adjusted after insertion of the stent into the blood vessel. Non-uniform stent expansion in this example occurs because the upper half of the stent wall that is constrained by semi-circular ring section members (such as 106) expands less than the lower half of the stent wall that is not so constrained. The location of the low-porosity upper portion is determined in situ, post-insertion, by the user through the selective removal of the lower ring section members (such as 107).

With respect to an innovative device, FIGS. 1-3 show an example of a stent with post-insertion determination of wall areas with differences in porosity comprising: a stent that is inserted into, and then expanded within, the parent vessel of an aneurysm, wherein the parent vessel is the blood vessel from which the aneurysm bulges; and one or more post-expansion cross-sectional perimeter differences in wall porosity, wherein a cross-sectional perimeter difference in wall porosity exists when the stent may be viewed as having at least one lateral cross-section and there are differences in porosity between two or more wall areas at different locations around the cross-sectional perimeter of this lateral cross section and wherein the locations on the stent wall of these one or more differences in cross-sectional perimeter wall porosity are selectively determined after the stent is inserted into the parent vessel, but before the stent is fully expanded within the parent vessel.

FIGS. 1-3 also show an example of a stent with one or more post-expansion cross-sectional perimeter differences in wall porosity. In FIGS. 1-3, the upper half of stent cross-sections has low porosity and the lower half of stent cross-sections has high porosity after non-uniform expansion.

FIGS. 1-3 also show an example of a stent wherein the locations on the stent wall of one or more post-expansion cross-sectional perimeter differences in wall porosity are selectively determined, after insertion of the stent, by the selective removal of one or more expansion-resisting members (including 107) among a plurality of expansion-resisting members (including 106 and 107), wherein these expansion-resisting members selectively restrict expansion of different areas, respectively, of the stent wall. In other examples, the locations on the stent wall of one or more post-expansion cross-sectional perimeter differences in wall porosity may be selectively determined, after insertion of the stent, by the selective detachment or stretching of one or more expansion-resisting members among a plurality of expansion-resisting members, wherein these expansion-resisting members selectively restrict expansion of different areas, respectively, of the stent wall. In FIGS. 1-3, the expansion-resisting members are the ring section members (including 106 and 107).

FIGS. 1-3 also show an example of a stent wherein the locations on the stent wall of one or more post-expansion cross-sectional perimeter differences in wall porosity are selectively determined, after insertion of the stent, by the selective detachment, removal, or stretching of one or more expansion-resisting members around a portion of the cross-sectional perimeter of a lateral cross section of the stent, selected from among a plurality of such expansion-resisting members around the cross-sectional perimeter of this lateral cross section.

In various examples, the selective detachment, removal, or stretching of one or more expansion-resisting members may be done using a means selected from the group consisting of: electrical energy, mechanical force, chemical process, thermal energy, ultrasonic energy, radio wave energy, infrared energy, ultraviolet energy, coherent light energy, or other light energy. In various examples, the selective detachment, removal, or stretching of one or more expansion-resisting members may be done using a means selected from the group consisting of: selective application of electrical energy in different locations or via different electrical circuits across the stent wall to melt or modify different expansion-resisting members; selective application of mechanical force to remove or modify different expansion-resisting members; selective application of chemicals in different locations or via different chemical processes to target different expansion-resisting members to dissolve or modify these different expansion-resisting members; or selective application of energy in different locations, at different frequencies, or of different types to selectively dissolve or modify different expansion-resisting members.

FIGS. 1-3 also show an example of a stent wherein the selective determination of the locations one or more differences in cross-sectional perimeter wall porosity changes the relative porosity of different areas of the expanded stent wall, but does not substantively change the overall shape of the expanded stent. The resulting stent is tubular despite differential wall porosity.

FIGS. 1-3 also show an example of a stent wherein the locations on the stent wall of one or more post-expansion cross-sectional perimeter differences in wall porosity are selectively determined after insertion of the stent by differential expansion of different areas of the stent wall. FIGS. 1-3 also show an example of a stent wherein the low-porosity area (the upper half) of the stent wall after expansion comprises approximately 50% of the total exterior surface area of the expanded stent wall. In various examples, at least one low-porosity area of the stent wall after expansion may comprise between 5% and 95% of the total exterior surface area of the expanded stent wall.

In contrast to customizing wall porosity in situ using non-uniform expansion, as just disclosed, the user could have tried to customize a stent with differential wall porosity prior to insertion of that stent into the blood vessel. However, as we discussed in our review of the prior art, there are a number of limitations with pre-insertion customization. For example, it can be challenging making a stent with the right configuration to match the configuration of the parent vessel (including the locations of the aneurysm neck and branching vessels) from outside the body based on remote imaging of tortuous vessels. Even if one could make such a stent to accurately match the configuration of the parent vessel, it is difficult to position a pre-configured stent in exactly the right location within the parent vessel. The distal ends of neurovascular guidewires and catheters are often curved, making it difficult to independently adjust the longitudinal and rotational placement of a stent. If a solid piece or folded graft is used to concentrate wall mass over the aneurysm neck, then the device may be insufficiently flexible to navigate tortuous intracranial vessels. If, alternatively, an expandable mesh is used, then it is difficult to concentrate enough mass over the aneurysm neck with uniform expansion. For these reasons, the ability to create variation in stent wall porosity in situ (post insertion), as disclosed in this invention, is a significant advance over creation of variation in stent wall porosity before insertion of the stent into the body.

In contrast to customizing wall porosity before expansion, as just disclosed, the user could have tried to customize a stent with differential wall porosity after expansion of that stent in the blood vessel. However, as we discussed in our review of the prior art, there are a number of limitations with post-expansion customization. For example, post-expansion wall customization is difficult to target in tortuous and hemodynamic blood vessels. For example, if post-expansion customization relies on activation of selected areas of the stent wall by targeting energy emissions to certain areas of the stent wall, then it can be challenging targeting energy only to the right places on the stent wall in tortuous vessels. This is especially true when the energy emitting or energy receiving mechanism is not integrated into the stent wall. Also, there can be risks of damage to the surrounding brain tissue from the energy emissions. If, alternatively, post-expansion customization is done by application of a chemical coating, then targeting of the coating to a particular area of the stent wall is also challenging. Also, coating chemicals can escape into general circulation throughout the body, with negative health effects. Finally, post-expansion customization of wall porosity does not allow the user to use non-uniform expansion to selectively concentrate the mass of a mesh over the aneurysm neck during mesh expansion.

Figure 4:
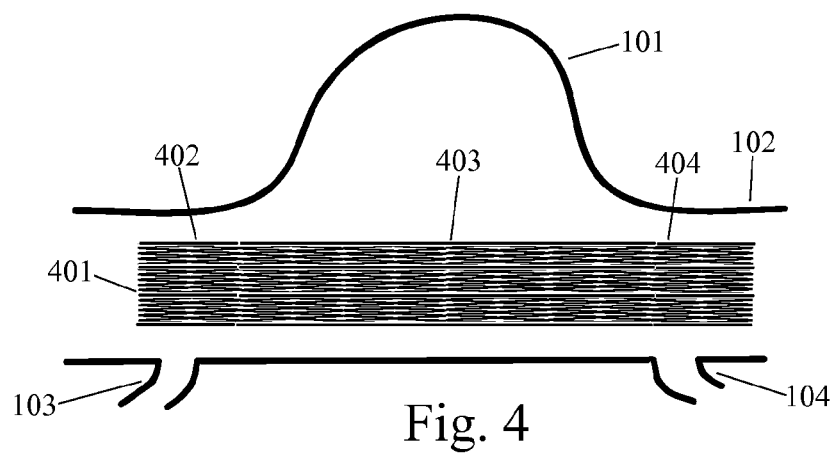
Figure 5:
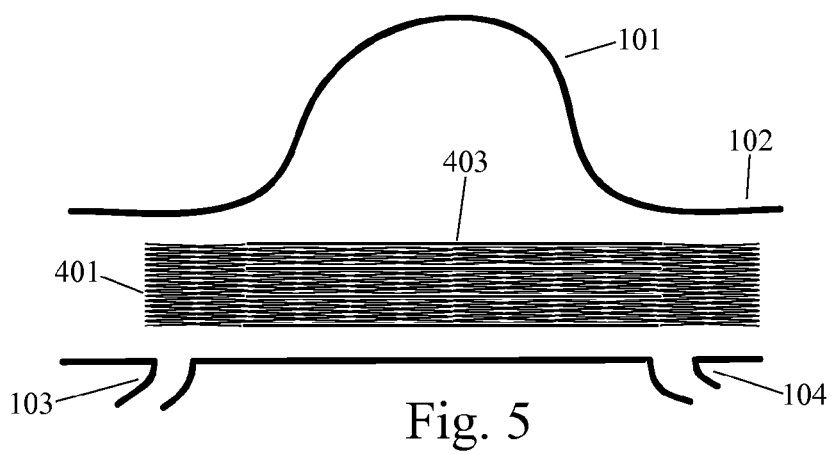
Figure 6:
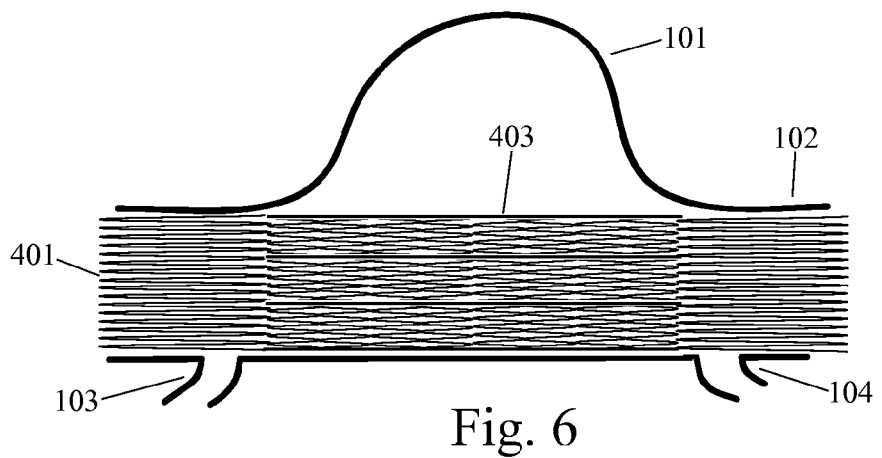

FIGS. 4-6 show another example of how this invention may be embodied to occlude this cerebral aneurysm without blocking blood flow to nearby branching vessels. The aneurysm, 101, parent vessel, 102, and branching vessels, 103 and 104, are the same as those introduced in FIGS. 1-3, but the way in which the invention is embodied is different. The configuration of differential wall porosity that is determined by a user in situ is different. In the example in FIGS. 4-6, the user creates a low-porosity wall area in a central longitudinal section of a generally-tubular stent that is deployed in the parent vessel. This low-porosity central longitudinal section of the stent wall substantially covers the aneurysm neck, thereby blocking blood flow to the aneurysm. The end sections of the stent wall have high porosity; they provide additional support for the low-porosity central longitudinal section, but do not block blood flow to branching blood vessels 103 and 104.

FIG. 4 shows a longitudinal cross-sectional view of aneurysm 101 bulging from parent vessel 102, as well as branching vessels 103 and 104. The entrances to these branching vessels are on the opposite side of the parent vessel from the aneurysm, but are not diametrically opposite the aneurysm neck. This variation in longitudinal spacing between the aneurysm neck and the entrances to the branching vessels is what allows the alternative form of differential wall porosity shown in FIGS. 4-6. This allows a solution based on longitudinal variation in wall porosity, in contrast to the solution based on cross-sectional variation in wall porosity that was shown in FIGS. 1-3. If the entrances to the branching vessels had been diametrically opposite the aneurysm neck, then only the solution based on cross-sectional variation in wall porosity in FIGS. 1-3 would work.

FIG. 4 shows longitudinal band members (including 402, 403, and 404) that collectively span the length of stent 105. Different bands span the stent over different points around the cross-sections of the stent. In this example, there are six bands spanning the stent. Four of these bands appear in this lateral view. In other examples, there may be a lesser or greater number of bands. In this example, there are three longitudinal band members in each band, including a central member (such as 403) and two end members (such as 402 and 404). In other examples, there may be a lesser or greater number of member in each band. In the extreme, the stent could have a closed cell design with a removable expansion-resisting member in each cell that resists longitudinal expansion.

Although the main body of stent 105 is made from an expandable mesh, the longitudinal band members (including 402, 403, and 404) resist expansion. In this example, the longitudinal band members (including 402, 403, and 404) are detachably attached to stent 105. The longitudinal bands collectively formed by the longitudinal band members constrain the longitudinal expansion of stent 105. Removal of all of the longitudinal band sections would allow the stent to lengthen uniformly. Selective removal of only some of the longitudinal bands in a longitudinal band causes the stent to expand longitudinally in a non-uniform manner. FIG. 4 shows stent 105 after it has been inserted into parent vessel 102, but before it has been expanded.

FIG. 5 shows the same stent as in FIG. 4, but after the longitudinal band members (including 402 and 404) on the two end sections of the stent have been selectively removed by the user. In this example, the longitudinal band members were removed by melting via selective application of electric current. Several methods of selectively melting portions of an implantable device with electric current are known in the prior art and the precise method is not central to this invention. In other examples, the longitudinal band members may be removed by chemical or manual means. The longitudinal band members in the central longitudinal section of stent 105 (including 403) remain attached to stent 105.

FIG. 6 shows this stent after it has been expanded, both cross-sectionally and longitudinally. In an example, the stent may be self-expanding when released from the expansion-resisting longitudinal band members. In another example, a stent may be expanded by inflation of a balloon inside it.

Since the expansion-resisting longitudinal band members had been selectively removed, as shown in FIG. 5, the stent has expanded longitudinally in a non-uniform manner. The central longitudinal section of stent 105, covering the neck of aneurysm 101, has been constrained by longitudinal band members (including 403) and has not expanded longitudinally. It only expanded cross-sectionally. However, the two end sections of stent 105, covering the entrances to branching vessels 103 and 104, were not constrained by longitudinal band members. Thus, these two end sections expanded longitudinally as well as cross-sectionally. The user determined this non-uniform longitudinal expansion in situ by the selective removal of longitudinal band members. The resulting expanded stent has a central longitudinal section with lower porosity that covers the aneurysm neck and two end sections with higher porosity that cover the entrances to the branching vessels.

With respect to a method disclosure, FIGS. 4-6 show another example of a method of creating differences in porosity between different areas of a stent wall comprising: inserting the stent into a blood vessel; and expanding the stent with non-uniform stent expansion, wherein non-uniform stent expansion is expansion in which different areas of the stent wall move different distances during stent expansion, wherein this non-uniform stent expansion causes one or more areas of the stent wall to have a lower porosity than the rest of the stent wall after stent expansion, and wherein the locations of these one or more areas, relative to the rest of the stent wall, can be determined or adjusted after insertion of the stent into the blood vessel. In FIGS. 4-6, non-uniform stent expansion occurs because the central longitudinal section of the stent wall that is constrained by longitudinal bands expands less (longitudinally) than the two end sections of the stent wall that are not so constrained. The locations of the low-porosity end sections were determined by the selective removal of the end portions of the longitudinal bands in situ by the user.

With respect to a device disclosure, FIGS. 4-6 show an example of a stent with post-insertion determination of wall areas with differences in porosity comprising: a stent that is inserted into, and then expanded within, the parent vessel of an aneurysm, wherein the parent vessel is the blood vessel from which the aneurysm bulges; and one or more post-expansion longitudinal differences in wall porosity, wherein a longitudinal difference in wall porosity exists when the stent may be viewed as having a longitudinal axis (which may be straight or curved) and there are differences in porosity between two or more wall areas at different locations along this longitudinal axis, and wherein the locations on the stent wall of these one or more differences post-expansion longitudinal differences in wall porosity are selectively determined after the stent is inserted into the parent vessel, but before the stent is fully expanded within the parent vessel.

FIGS. 4-6 also show an example of a stent wherein the locations on the stent wall of one or more post-expansion longitudinal differences in wall porosity are selectively determined, after insertion of the stent, by the selective removal of one or more expansion-resisting members among a plurality of expansion-resisting members, wherein these expansion-resisting members selectively restrict expansion of different areas, respectively, of the stent wall. In other examples, the locations on the stent wall of one or more post-expansion longitudinal differences in wall porosity may be selectively determined, after insertion of the stent, by the selective detachment or stretching of one or more expansion-resisting members among a plurality of expansion-resisting members, wherein these expansion-resisting members selectively restrict expansion of different areas, respectively, of the stent wall. In FIGS. 4-6, the expansion-resisting members are the longitudinal band members.

FIGS. 4-6 also show an example of a stent wherein the locations on the stent wall of one or more post-expansion longitudinal differences in wall porosity are selectively determined, after insertion of the stent, by the selective detachment, removal, or stretching of one or more expansion-resisting members that each span a portion of the length of the stent, selected from among a plurality of such expansion-resisting members spanning the length of the stent. FIGS. 4-6 show an example of a stent with one or more post-expansion longitudinal differences in wall porosity. In FIGS. 4-6, the central longitudinal portion of the stent has low porosity and the end portions of the stent have high porosity after non-uniform expansion.

FIGS. 4-6 also show examples of a stent wherein the selective determination of the locations one or more post-expansion longitudinal differences in wall porosity changes the relative porosity of different areas of the expanded stent wall, but does not substantively change the overall shape of the expanded stent. The resulting stent is tubular in this example despite changes in differential wall porosity. FIGS. 4-6 show examples of a stent wherein only the locations on the stent wall of one or more post-expansion longitudinal differences in wall porosity are selectively determined after insertion of the stent by differential expansion of different areas of the stent wall. In other examples, both post-expansion cross-sectional perimeter differences in wall porosity and post-expansion longitudinal differences in wall porosity may be selectively determined after insertion of the stent.

FIGS. 4-6 also show an example wherein the low-porosity area (central longitudinal segment) of the stent wall after expansion comprises approximately 60% of the total exterior surface area of the expanded stent wall. In various examples, at least one low-porosity area of the stent wall after expansion may comprise between 5% and 95% of the total exterior surface area of the expanded stent wall.

Figure 7:
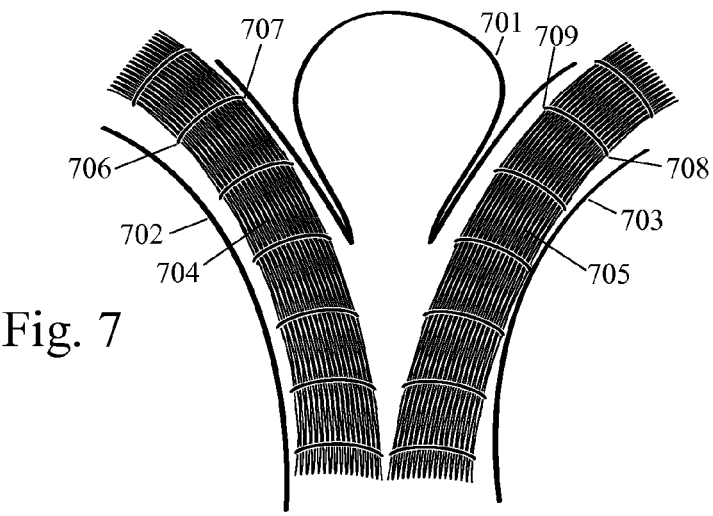
Figure 8:
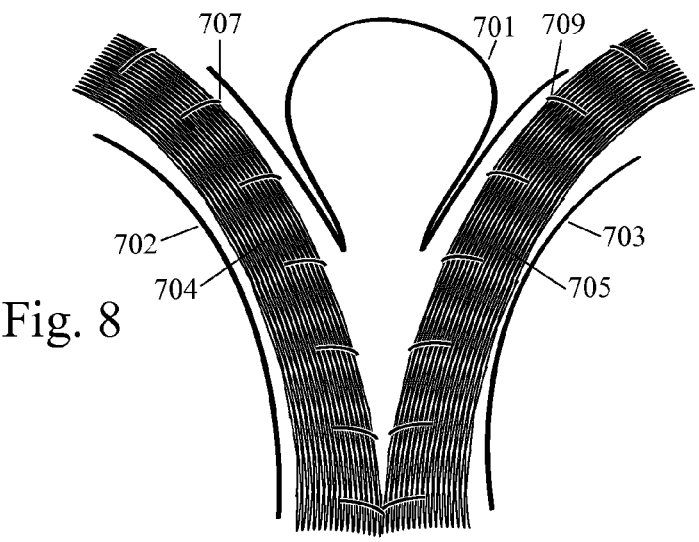
Figure 9:
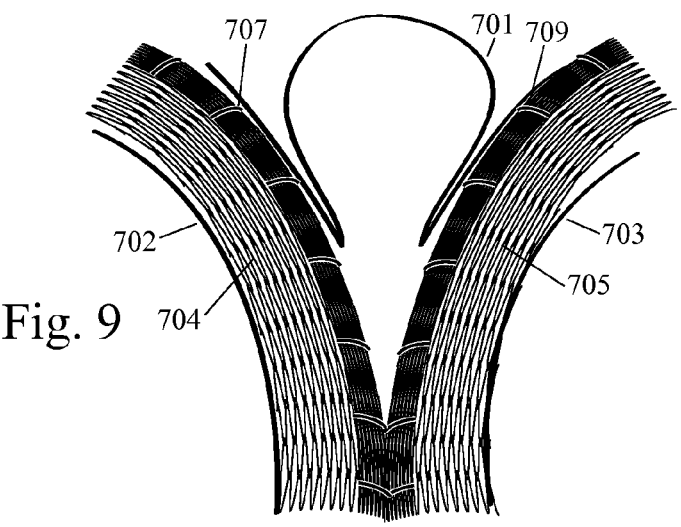

FIGS. 7-9 show an example of how this invention may be embodied in a pair of stents to treat an aneurysm that has formed at the juncture of a fork in the vasculature with two branching blood vessels. Such an embodiment can be useful for occluding aneurysms in the Circle of Willis. FIG. 7 shows a saccular aneurysm 701 that has formed at the juncture of branching vessels 702 and 703. FIG. 7 further shows two separate stents, 704 and 705, that have been inserted into vessels 702 and 703, respectively, spanning the juncture. The distal (upper in this case) ends of stents 704 and 705 are within vessels 702 and 703 and the proximal (lower in this case) ends of stents 704 and 705 are within the pre-branching vessel. In this example, these two stents, 704 and 705 have been inserted sequentially. In another example, these two stents may be inserted simultaneously. FIG. 7 shows these stents after they have been inserted, but before they have been expanded.

In a manner similar to the stent shown in FIGS. 1-3, stents 704 and 705 are each comprised of an expandable tubular mesh that is constrained with respect to cross-sectional expansion by a series of ring section members that encircle the perimeter of different cross-sections of the stents. In this example, stent 704 is cross-sectionally constrained by five cross-sectional rings (or "hoops") formed by removable semi-circular ring section members, including ring section members 706 and 707. Similarly, stent 705 is cross-sectionally constrained by five cross-sectional rings (or "hoops") formed by removable semi-circular ring section members, including ring section members 708 and 709.

In this example, the ring section members are semi-circular. Each of them spans 180 degrees of the circular perimeter of a stent cross-section. In another example, the ring section members may each be quarter-circles and span 90 degrees. In other examples, the ring section members may each span a smaller arcuate portion (e.g. 60 degrees, or 45 degrees, or less) of the perimeter of a cross-section of the stent. In the extreme, the expandable stent mesh may have a closed cell design in which each cell has its own removable expansion-resisting member, thus allowing very precise determination of the configuration of non-uniform expansion in situ. There is a trade-off between the increased manufacturing complexity of having a greater number of removable ring section members per cross-section and the increased accuracy in configuration enabled by having a greater number of removable ring section members per cross-section.

FIG. 8 shows this pair of stents (704 and 705) after the ring section members (including 706 and 708, respectively) on their sides that face away from the vessel juncture have been removed. Only the ring section members (including 707 and 709, respectively) remain attached to the main bodies of stents 704 and 705. As discussed with respect the embodiments disclosed in FIGS. 1-3 and FIGS. 4-6, in various examples the ring section members may be removed using electrical current, chemical processes, or manual extraction. As also previously discussed, stents 704 and 705 may be self-expanding or may be expanded by the inflation of balloons inside them. In this example, such inflation is simultaneous. In another example, such inflation could be sequential.

With a greater number of removable ring section members per cross-section, precise rotational positioning of these stents in the vessels becomes less important. With a large number of selectively removable ring sections, one can position the stents in the vessels in virtually any rotational configuration and still configure them such that the portions of their expansion-resisting rings that face away from the vessel juncture are removed. For example, suppose that these stents, 704 and 705, were placed into vessels 702 and 703, respectively, with the "wrong" rotational configurations. Suppose that ring section members 707 and 709 faced away from the vessel juncture rather than towards the vessel juncture. If the low and high porosity areas of these stents were pre-determined based on pre-insertion construction, then this would be a problem. The user would have to try to rotate these stents into the proper rotational positions. Given confounding of longitudinal and rotation placement by the curved nature of the distal ends of neurovascular guidewires and catheters, this could be difficult.

However, the "wrong" rotational configuration is not a problem with the presently-disclosed invention. Non-uniform expansion can be adjusted in situ. Especially when there are several expansion-resisting members per cross-section, adjustment becomes independent of the actual rotational placement of the stent. Back to this specific example, even if the stents were placed into the vessels with the "wrong" rotational configuration and it were very difficult for the user to rotate them without corrupting longitudinal alignment, then the user can simply chose to remove ring section members (707 and 709) instead of ring section members 706 and 708. The net result would be that both stents would still expand as originally intended. This is one of the advantages of the in situ post-insertion determination of differential wall porosity that is enabled by this present invention.

FIG. 9 shows this pair of stents, 704 and 705, after they have been expanded. Due to the in situ selective removal of expanding-resisting cross-sectional ring members by the user, these stents have differential post-expansion wall porosity. The sides of these stents that face the vessel juncture, where the aneurysm is, have low wall porosity (because of ring section member constraint during expansion) and the sides of these stents that face away from the vessel juncture have high wall porosity (because of lack of ring section member constraint during expansion). The resulting configuration of these two stents is particularly advantageous because it selectively blocks blood flow to aneurysm 701, allows blood flow to branching vessels 702 and 703, and provides good structural support for the combined stent configuration. With respect to structural support, the two stents, 704 and 705, are firmly held in the branching vessels 702 and 703 because they expand to fill the entire vessel circumferences, over substantive longitudinal segments, of these vessels. This provides a solid structural base for the wedge-shaped low-porosity area that diverts blood away from the aneurysm. This is an advantage over stand-alone aneurysm patches that rely on less-substantive loops or weak structural supports within the vessel juncture to hold them in place over the aneurysm neck.

The wedge shape of the low-porosity area provided by this embodiment is also an advantage with respect to correcting the flow dynamics in the parent vessel that may have contributed to the formation of the aneurysm in the first place. The wedge shape diverts blood away from the aneurysm neck in a more gradual manner than a relatively flat aneurysm patch that goes straight across the neck of the aneurysm. A relatively flat patch that goes straight over the aneurysm neck can be subjected to, and weaken from, the same fluid pulse "hammering" effect that created the aneurysm at the juncture in the first place. In contrast, the wedge-shaped low-porosity area that is created by this embodiment provides a superior blood flow diverter. It can greatly reduce the fluid "hammering" effect on the aneurysm neck. For these reasons, the aneurysm may be less likely to grow, and be more likely to be therapeutically embolized, with this present invention than with many of the aneurysm patches in the prior art that are intended to treat aneurysms in the Circle of Willis.

FIGS. 10-12 provide a lateral close-up view of another embodiment of this invention. This embodiment is a stent with a relatively large number of removable small-scale expansion-resisting members that are incorporated into the mesh of the stent wall. This design offers relatively fine in situ control over determination of post-expansion differential wall porosity. In this example, the selectively-removable expansion-resisting members are generally cross-sectionally circumferential in orientation, each spanning a portion of the cross-sectional perimeter. This allows the user to create differences in wall porosity around different areas of cross-sectional perimeters.

FIG. 10 shows aneurysm 1001 protruding from parent vessel 1002, with the entrance to branching vessel 1003 located diametrically opposite the aneurysm neck. FIG. 10 also shows stent 1004 with an expandable mesh that includes a number of partially circumferential expansion-resisting members, including 1005 and 1006. In FIG. 10, the stent has been inserted into parent vessel 1002, but not yet expanded. FIG. 11 shows this same aneurysm and stent after the expansion-resisting members, including 1006, on the lower half of the stent wall have been removed. In this example, these members have been selectively removed by melting using electrical current. In other examples, these members may be selectively removed by other methods such as chemical processes or manual extraction. In this example, one or more areas of the stent wall stretch during expansion.

FIG. 12 shows the stent after non-uniform expansion. Stent expansion is non-uniform because expansion of the top portion of the stent wall is constrained by expansion-resisting members, including 1005, but the bottom portion of the stent wall is not constrained. The result is a stent with differential wall porosity. Specifically, the stent wall has low porosity over the aneurysm neck and high porosity over the entrance to the branching vessel.

Figure 13:
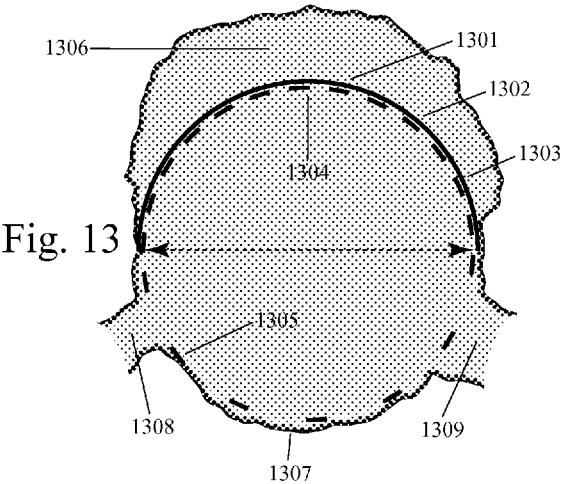
Figure 14:
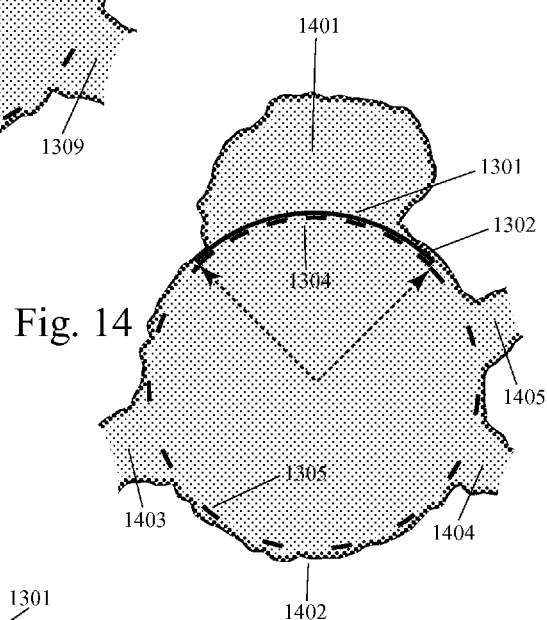
Figure 15:
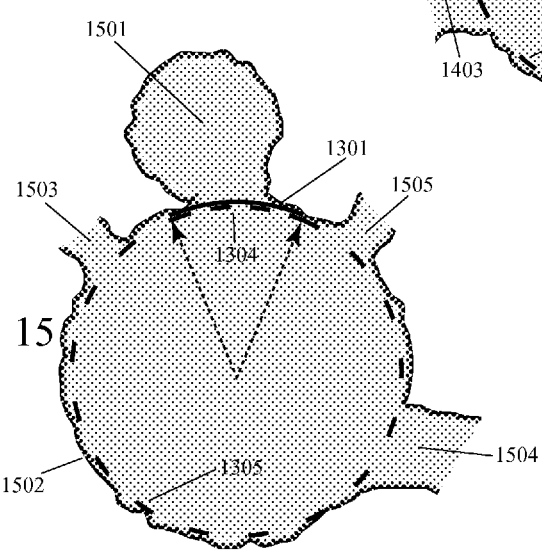

FIGS. 13-15 show, in detail, three examples of how this invention can enable a user to adjust, in situ, the arcuate portion of a cross-sectional perimeter of the stent wall that will become low-porosity during expansion of the stent. This constitutes advanced in situ tailoring of stent wall porosity to the unique features of vessel anatomy in a manner that does not seem to be offered by the prior art. Features that can be considered in this in situ tailoring include the size and location of the aneurysm neck and the size and locations of entrances to nearby branching vessels. This invention allows a user to adjust the number of degrees of a circular cross-sectional perimeter of the stent's wall that will become low-porosity after expansion. If the aneurysm neck is wide, then the user can adjust the low porosity area to cover a wide portion of the stent wall cross-section. If the aneurysm neck is narrow, then the user can adjust the low porosity area to only cover a narrow portion of the stent wall cross-section. Selection of how many degrees of the stent's cross-sectional perimeter will be low porosity can also be influenced by the number and location of nearby branching vessels. FIGS. 13-15 show three examples, respectively, of how the same stent can be selectively tailored in situ with differential wall porosity to fit three different vessel and aneurysm configurations.

FIG. 13 shows the first example of such in situ tailoring of differential stent wall porosity. FIG. 13 shows a cross-sectional view of a parent vessel, 1307, with an aneurysm, 1306, whose neck spans almost 180 degrees (the upper semi-circle) of the parent vessel wall. FIG. 13 also shows two branching vessels, 1308 and 1309, which exit the parent vessel from the same cross-section as the aneurysm. Such a wide-neck aneurysm would be challenging to clip surgically. It also would be difficult to occlude with coils alone. Further, it would be tough to treat such a configuration with a stent in the parent vessel, unless the stent were to have differential wall porosity. Ideally, one would like a stent with differential wall porosity to block blood flow into aneurysm neck without blocking blood flow into the branching vessels. This invention not only provides such a stent, but it allows the user to tailor the stent, in situ, to the specifics of the vessel anatomy.

FIG. 13 also shows a post-expansion cross-sectional view of a tubular stent comprising a mesh (represented by a circular dashed line 1304 and 1305) and expansion-resisting ring section members (including 1301, 1302, and 1303). The ring section members on the bottom portion of the stent mesh (1305) have been removed by the user, so that only the ring section members (including 1301, 1302, and 1303) on the top portion of the stent mesh (1304) remain. FIG. 13 shows the stent after it has been expanded. As we have discussed for prior figures, the selective removal of expansion-resisting members causes non-uniform expansion which causes different wall porosity. In this example, the selective removal of expansion-resisting ring section members from the bottom portion of the stent mesh (1305) has resulted in low porosity mesh (1304) covering the aneurysm neck and high porosity mesh (1305) covering the branching vessels. The denser dashes in the upper half of the stent mesh (1304) graphically represent lower wall porosity and the less-dense dashes in the lower half of the stent mesh (1305) represent higher wall porosity. As shown by the central dashed arrows in FIG. 13, the selective removal of ring section members in FIG. 13 has resulted in a low-porosity area that spans the approximately 180-degree (semi-circular) upper half of the stent cross-section that covers the aneurysm neck.

FIG. 14 shows a second example of such in situ tailoring of differential stent wall porosity. FIG. 14 shows a cross-sectional view of a different parent vessel, 1402, with an aneurysm, 1401, whose neck spans approximately 90 degrees (the upper quarter-circle) of the vessel wall. FIG. 14 also shows three branching vessels (1403, 1404, and 1405) which exit the parent vessel from different locations around the same cross-sectional perimeter as the aneurysm. It would be tough to treat such a configuration with a stent in the parent vessel, unless the stent were to have differential wall porosity. This invention provides such a stent that allows the user to tailor the stent, in situ, to the specifics of this vessel anatomy.

FIG. 14 also shows a post-expansion cross-sectional view of the same stent that was introduced in FIG. 13, except that its post-expansion wall porosity is now different. Its post-expansion wall porosity has been tailored to this new vessel configuration, in situ, by the user's selective removal of expansion-resisting ring section members. In FIG. 14, only the ring section members (including 1301 and 1302) on the upper quarter-circle of the cross-section perimeter have been left attached to the stent. Unlike the case in FIG. 13, ring section member 1303 and its symmetric counterpart have been removed to tailor the stent to the configuration of this second vessel. As a result, the upper portion (1304) of the stent mesh is low porosity and the bottom portion (1305) is high porosity. The stent's wall porosity has been tailored, in situ, to the unique configuration of this vessel's anatomy. As shown by the dashed arrows in FIG. 14 (that look like clock hands), the selective removal of ring section members in FIG. 14 has resulted in a low-porosity area that spans the approximately 90-degree (quarter-circle) portion of the stent cross-section that covers the aneurysm neck.

FIG. 15 shows a third example of such in situ tailoring of differential stent wall porosity. FIG. 15 shows a cross-sectional view of a different parent vessel, 1502, with an aneurysm, 1501, whose neck spans only around 45 degrees of the vessel wall. FIG. 15 also shows three branching vessels (1503, 1504, and 1505) which exit the parent vessel from different locations around the same cross-sectional perimeter as the aneurysm. It would be tough to treat such a configuration with a stent with uniform wall porosity in the parent vessel. This invention provides a stent that allows the user to tailor the wall porosity of the stent, in situ, to the specifics of this vessel anatomy.

FIG. 15 also shows a post-expansion cross-sectional view of the same stent that was shown in FIGS. 13-14, except that now its post-expansion wall porosity is different. In FIG. 15, only the top-most ring section members (including 1301) have been left attached to the stent. Ring section members 1303 and 1304 (and their symmetric counterparts) have been removed to tailor the stent to the configuration of this third vessel. As a result, the upper portion (1304) of the stent mesh is low porosity and the bottom portion (1305) is high porosity. The stent's wall porosity has been tailored, in situ, to the unique configuration of this vessel's anatomy. As shown by the dashed arrows in FIG. 15 (that look like clock hands), the selective removal of ring section members in FIG. 15 has resulted in a low-porosity area that spans the approximately 45-degree section of the stent cross-section that covers the aneurysm neck.

Overall, FIGS. 13-15 show how the portion of a cross-sectional perimeter of the stent wall that will become low-porosity during expansion of the stent can be adjusted in situ, after the stent has been inserted into a blood vessel but before the stent has been expanded within that blood vessel.

Figure 16:
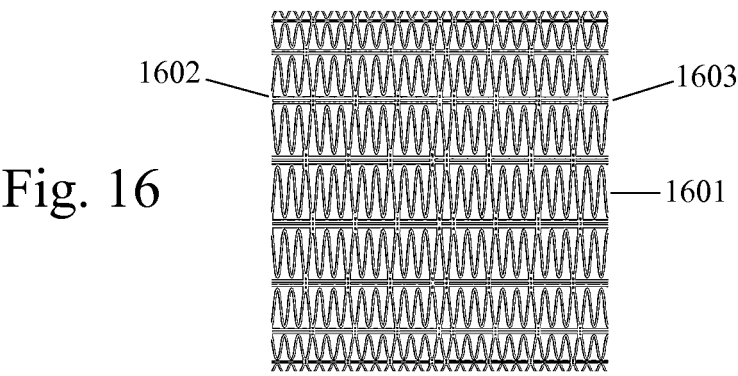
Figure 17:
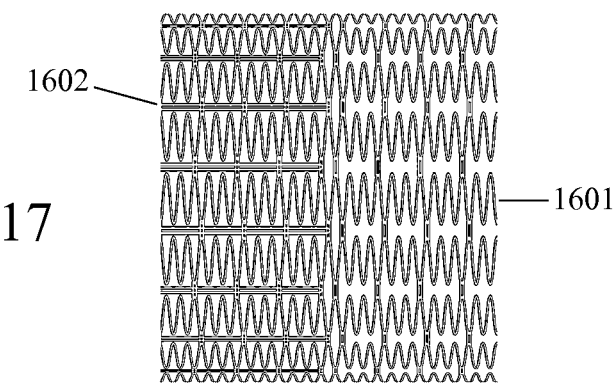
Figure 18:
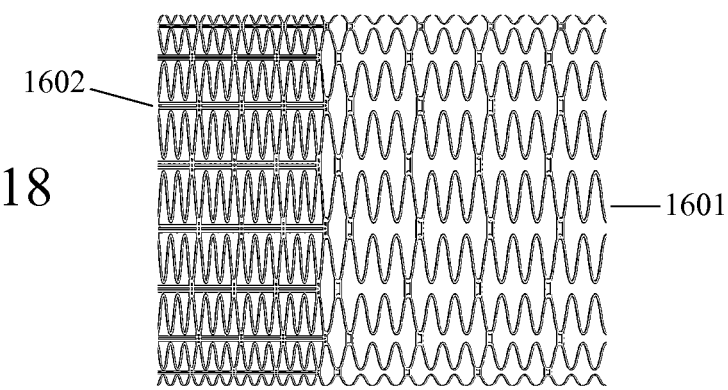

FIGS. 16-18 show a lateral close-up view of an example of non-uniform longitudinal mesh expansion (and resulting longitudinal differences in wall porosity) caused by selective in situ removal of longitudinal expansion-resisting members. This example may be seen as the longitudinal non-uniform expansion counterpart to the example of cross-sectional non-uniform expansion that was shown in FIGS. 10-12. As in FIGS. 10-12, this example is a stent with a relatively large number of removable small-scale expansion-resisting members that are incorporated into the mesh of the stent wall. This offers relatively fine in situ control over determination of post-expansion differential wall porosity. In this example, the expansion-resisting members are generally longitudinal in orientation, allowing the user to create post-expansion differences in wall porosity between different longitudinal segments of the stent.

FIG. 16 shows a stent with an expandable mesh 1601 and a number of longitudinal expansion-resisting members, including 1602 and 1603. FIG. 17 shows this same stent after the expansion-resisting members, including 1603, on the right half of the stent wall have been removed by melting using electrical current, but before stent expansion. FIG. 18 shows this same stent after non-uniform expansion. Stent expansion in this example is non-uniform because expansion of the left half of the stent wall is constrained by expansion-resisting members, including 1602, but the right half of the stent wall is not so constrained. The result is a stent with longitudinally differential wall porosity.

Examples of the invention shown thus far, in FIGS. 1-18, demonstrate how this invention may be used: to create stents with removable ring segment expansion-resisting members that allow in situ determination of cross-sectional perimeter variation wall porosity; or to create stents with removable longitudinal band expansion-resisting members that allow in situ determination of longitudinal variation in wall porosity. Now FIGS. 19-22 show how a closed-cell mesh embodiment of this invention can allow in situ determination of cross-sectional porosity variation, longitudinal porosity variation, or both cross-sectional and longitudinal porosity variation—from the same stent.

Figure 19:
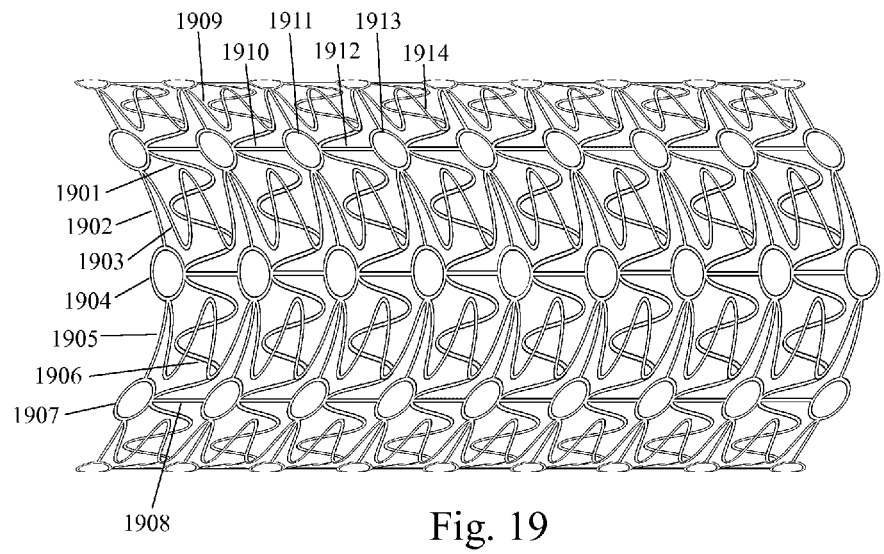

FIG. 19 gives a side view of a tubular stent with a closed-cell mesh design before it is expanded. Each of the cells comprising this mesh includes: an intra-cell cross-sectionally expandable member; intra-cell cross-sectionally expansion-resisting members; an intra-cell longitudinal expandable member; and intra-cell longitudinal expansion-resisting members. In FIG. 19, the intra-cell cross-sectionally expandable members include sinusoidal members 1901 and 1906. The intra-cell cross-sectionally expansion-resisting members include straight connectors 1902 and 1905. The intra-cell longitudinal expandable members include sinusoidal members 1903, 1909, and 1914. The intra-cell longitudinal expansion-resisting members include straight connectors 1908, 1910 and 1912. Inter-cell connectors include circles 1904, 1907, 1911, and 1913.

In situ selective removal of cross-sectionally expansion-resisting members and/or longitudinal expansion-resisting members from these cells causes non-uniform expansion, which in turn causes cross-sectional and/or longitudinal variation in post-expansion wall porosity. With the ability to selectively remove the expansion-resisting members from any cell, or group of cells, a user has considerable in situ ability to tailor differences in the stent's post-expansion wall porosity to the specific anatomic configuration of the blood vessel in which it is deployed.

Figure 20:
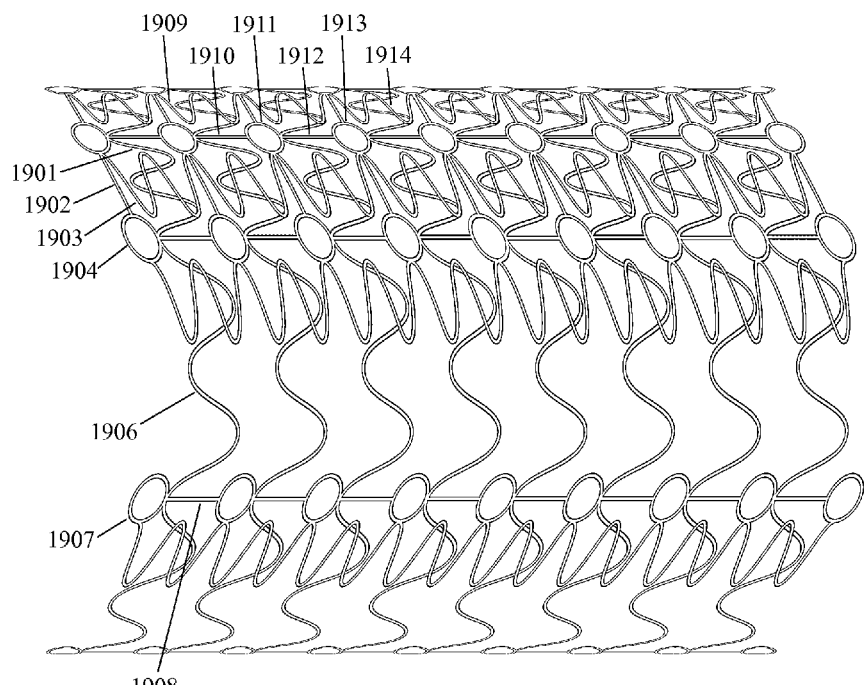

FIG. 20 gives a side view of this same tubular stent, after the intra-cell cross-sectionally expansion-resisting members (including 1905) in cells on the bottom half of the stent have been removed in situ and after the resulting non-uniform expansion of the stent. During this non-uniform expansion, cells from which the intra-cell cross-sectionally expansion-resisting members have been removed have expanded cross-sectionally. Cells that have been thus expanded form an area of the stent wall with higher porosity. In this example, the entire bottom half of the stent wall has higher porosity. During this non-uniform expansion, cells from which the intra-cell cross-sectionally expansion-resisting members have not been removed have not expanded cross-sectionally. Their arcuate profile may have widened, but their mesh density and porosity have not changed from what they were in the pre-expansion stent state. In this example, the entire top half of the stent wall has lower porosity.

Figure 21:
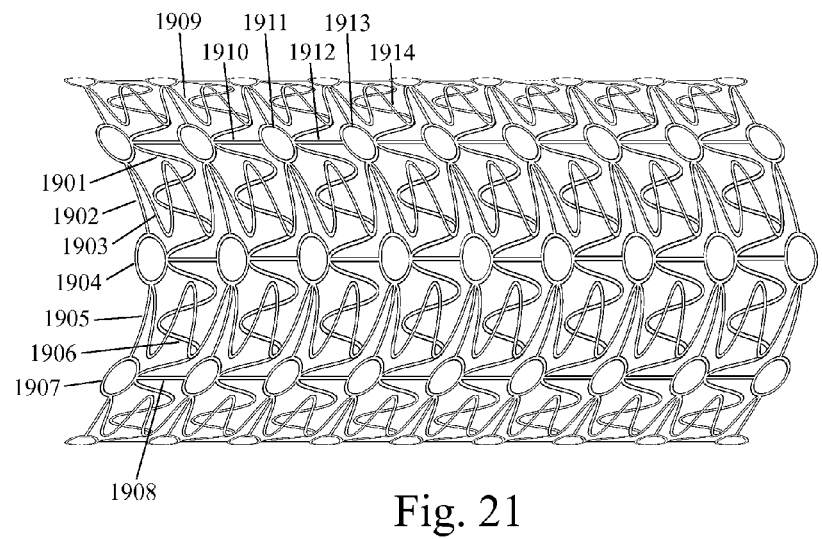
Figure 22:
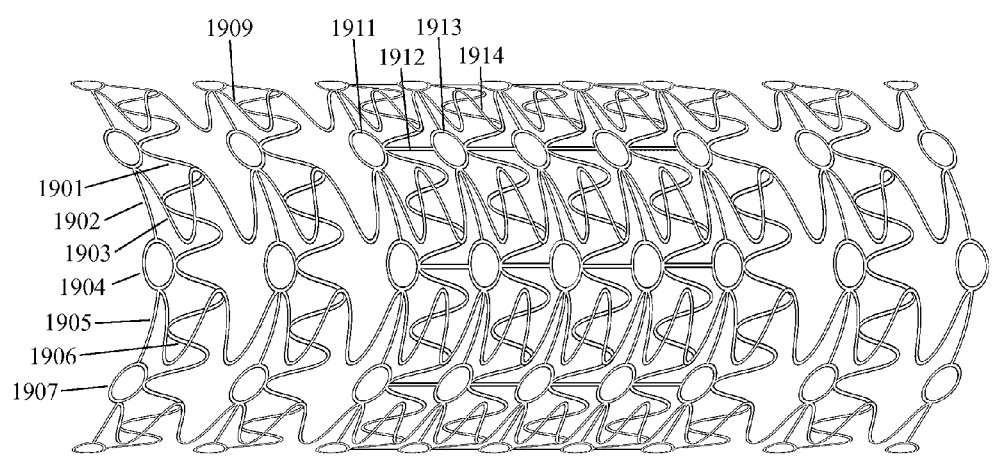

FIG. 21 is a repeat of FIG. 19 to provide same-page comparison of selective longitudinal expansion in FIG. 22. FIG. 22 gives a side view of this same tubular stent, after intra-cell longitudinal expansion-resisting members (including 1908 and 1910) in cells on the left and right end segments of the stent have been removed in situ and after the resulting non-uniform expansion of the stent. During this non-uniform expansion, cells from which the intra-cell longitudinal expansion-resisting members have been removed have expanded longitudinally. Cells that have been thus expanded form areas of the stent wall with higher porosity. In this example, the left and right end segments of the stent wall have higher porosity. During this non-uniform expansion, cells from which the intra-cell longitudinal expansion-resisting members have not been removed have not expanded longitudinally. Their mesh density and porosity have not changed from what they were in the pre-expansion stent state. In this example, the central longitudinal segment has lower porosity.

In the examples shown in FIGS. 19-22, either cross-sectional or longitudinal expansion-resisting members were selectively removed from certain closed cells. In another example using this same closed-cell stent design, both cross-sectional and longitudinal expansion-resisting members may be selectively removed from certain cells. In this latter example, the user can determine simultaneous cross-sectional and longitudinal differences in post-expansion wall porosity. In an example, a stent wall can include both expandable members and expansion-resisting members, in both longitudinal and cross-sectional orientations, wherein post-expansion cross-sectional perimeter differences in wall porosity, post-expansion longitudinal differences in wall porosity, or both such differences in wall porosity can be selectively determined after insertion of the stent into the parent vessel but before the stent is fully expanded by the selective detachment, removal, or stretching of one or more expansion-resisting members.

In an example, a stent wall can have one or more closed cells with both expandable members and expansion-resisting members, in both longitudinal and cross-sectional orientations, wherein post-expansion cross-sectional perimeter differences in wall porosity, post-expansion longitudinal differences in wall porosity, or both such differences in wall porosity can be selectively determined after insertion of the stent into the parent vessel but before the stent is fully expanded by the selective detachment, removal, or stretching of one or more expansion-resisting members in these cells.

FIGS. 23-30 show examples of how this invention may be embodied using multiple inflatable members to create non-uniform stent expansion. These figures show examples wherein the locations on the stent wall of one or more post-expansion cross-sectional perimeter differences in wall porosity or post-expansion longitudinal differences in wall porosity are selectively determined, after insertion of the stent, by the selective inflation of one or more inflatable members among a plurality of inflatable members, or a plurality of chambers in a single inflatable member, wherein these inflatable members or chambers selectively expand different areas, respectively, of the stent wall.

Figure 23:
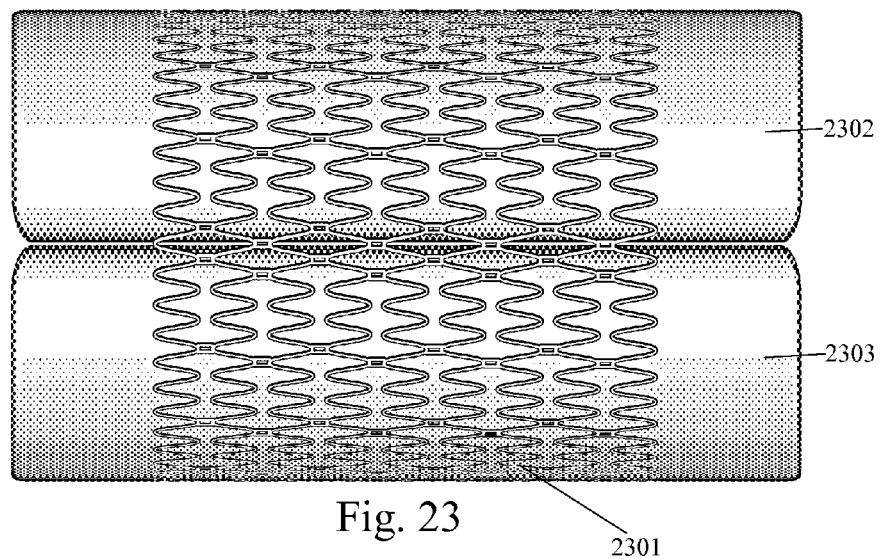
Figure 24:
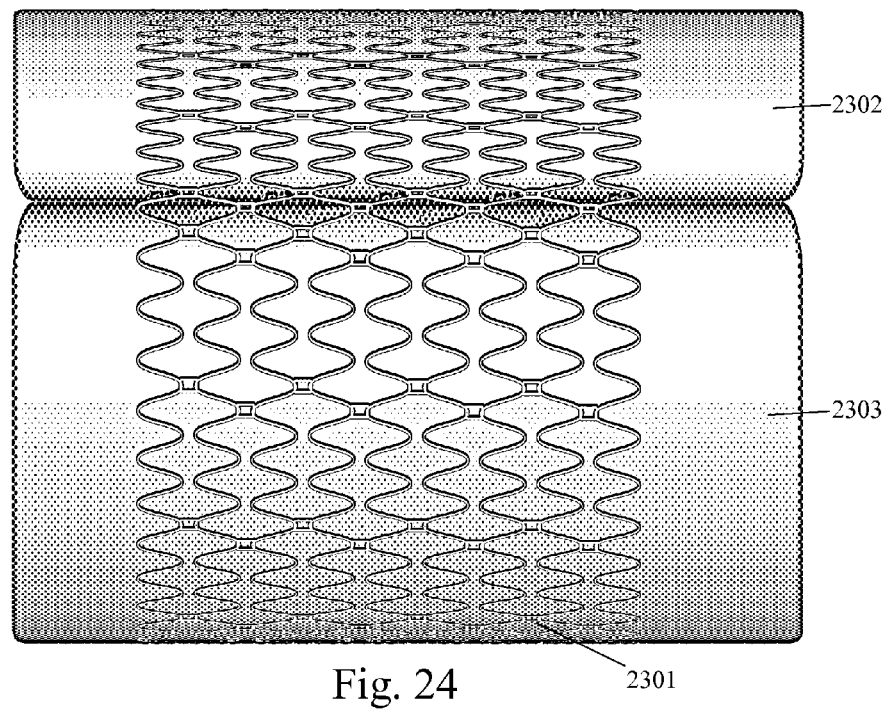

FIG. 23 shows a lateral side view of two parallel longitudinal inflatable members, 2302 and 2303, inside expandable mesh stent 2301. FIG. 23 shows this stent after insertion into a blood vessel, but before expansion. FIG. 24 shows expandable mesh 2301 after it has been non-uniformly expanded by differential inflation of inflatable member 2303 more than inflatable member 2302. In this example, inflatable member 2302 has not been inflated at all. In another example, inflatable member 2302 may be inflated somewhat, but not as much as inflatable member 2303. In FIG. 24, differential inflation of 2303 more than 2302 has caused the bottom half of the expandable mesh 2301 to expand more than the top half of expandable mesh 2301. In this example, the stent does not substantially contract after being expanded. After the inflatable members are deflated and removed, the stent has lower porosity in its upper half and higher porosity in its lower half Although the stent is not shown in the context of an aneurysm and branching vessels, as in previous figures, it is clear that the ability to determine such differential wall porosity in situ can be used to cover an aneurysm neck with a lower porosity area of the stent wall and cover branching vessels with a higher porosity area of the stent wall.

In the example shown in FIGS. 23-24, the locations on the stent wall of one or more post-expansion cross-sectional perimeter differences in wall porosity are selectively determined by the selective, differential, or sequential inflation of one or more inflatable members that each have a lateral cross section that spans a portion of the interior of a lateral cross section of the stent, selected from among a plurality of such inflatable members spanning the interior of this lateral cross section.

Figure 25:
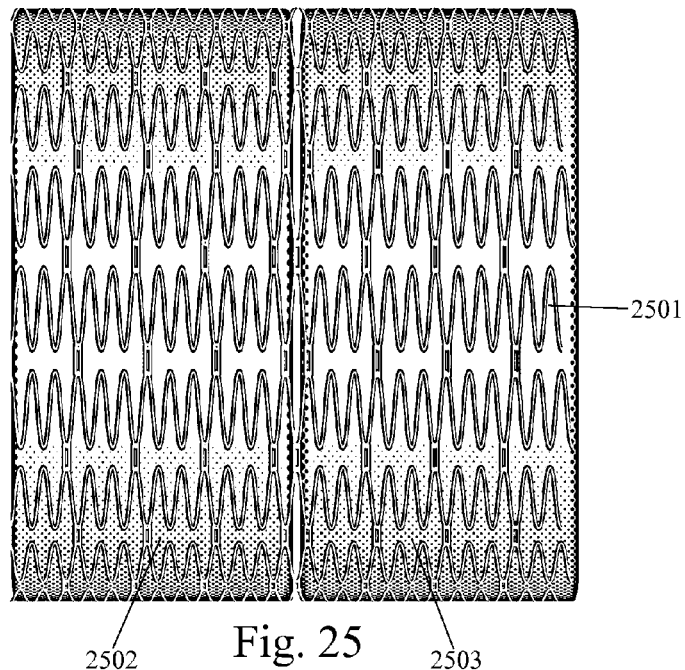
Figure 26:
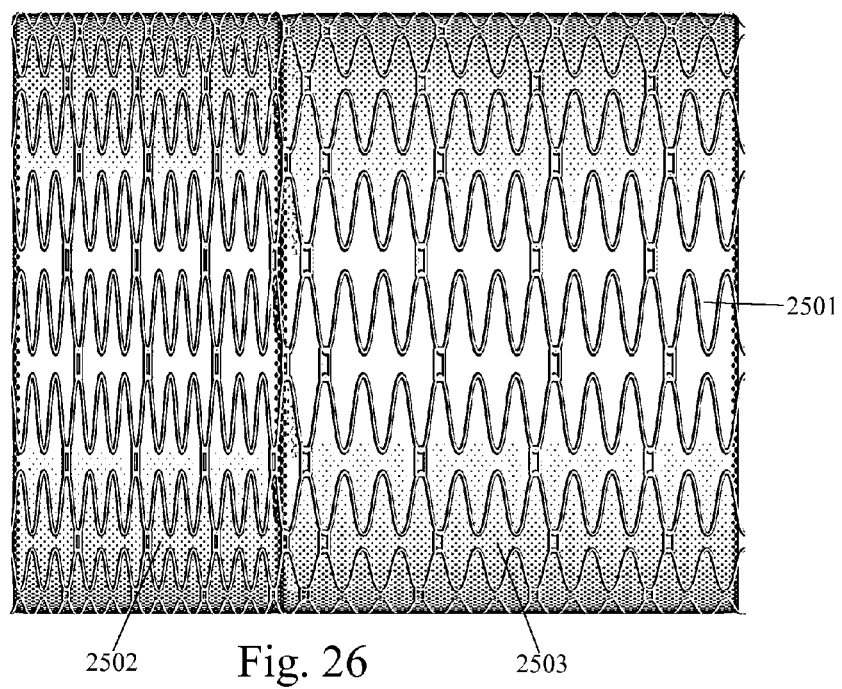

FIG. 25 shows a side view of a longitudinal series of inflatable members, 2502 and 2503, inside expandable mesh stent 2501. FIG. 25 shows this stent after insertion into a blood vessel, but before expansion. FIG. 26 shows how the expandable mesh has been non-uniformly expanded by differential inflation of inflatable member 2503 more than inflatable member 2502. Differential inflation of 2503 more than 2502 has caused the right half of the expandable mesh 2501 to expand more than its left half After the inflatable members are deflated and removed, the stent will have higher porosity in its right half and lower porosity in its left half. In this example, the locations on the stent wall of one or more post-expansion longitudinal differences in wall porosity are selectively determined by the selective, differential, or sequential inflation of one or more inflatable members that each span a portion of the length of the stent, selected from among a plurality of such inflatable members spanning the length of the stent.

In the example shown in FIGS. 25-26, the location on the stent wall of one or more post-expansion cross-sectional perimeter differences in wall porosity or post-expansion longitudinal differences in wall porosity are selectively determined after insertion of the stent by the selective inflation of one or more inflatable members with non-uniform radial expansion among a plurality of inflatable members, or a plurality of chambers in a single inflatable member, wherein these inflatable members or chambers selectively expand different areas, respectively, of the stent wall.

In the examples shown in FIGS. 23-26, the inflatable members are balloons. In various examples, the inflatable members may be made from one or more of the following materials: Ethylene Propylene Diene Monomer (EPDM), latex, silicone, PolyTetraFluoroEthylene (PTFE), polyvinyl chloride, and polyurethane. In this example, the inflatable members have uniform wall elasticity. Their differential expansion is based on differences in inflationary pressure, not differences in wall elasticity. In another example, the inflatable members may have non-uniform inter-member wall elasticity or intra-member wall elasticity. Their differential expansion may be based on differences in wall elasticity, not differences in inflationary pressure.

In these examples, both inflatable members are inflated by a gas. In another example, both inflatable members may be expanded by a fluid. In another example, one inflatable member may be inflated by a gas and another inflatable member may be expanded by a fluid. In this example, the inflatable members are not attached to each other. In another example, the inflatable members may be attached to each other to influence their non-uniform expansion. In these examples, there are two inflatable members. In other examples, there may be more than two inflatable members. In these examples, the two inflatable members are two separate balloons. In another example, there may be a single balloon with two (or more) chambers. In these examples, differential inflation creates non-uniform expansion which creates cross-sectional perimeter differential wall porosity.

Figure 27:
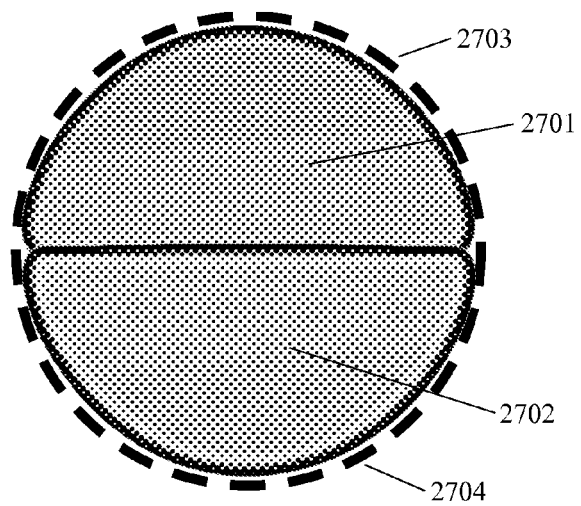
Figure 28:
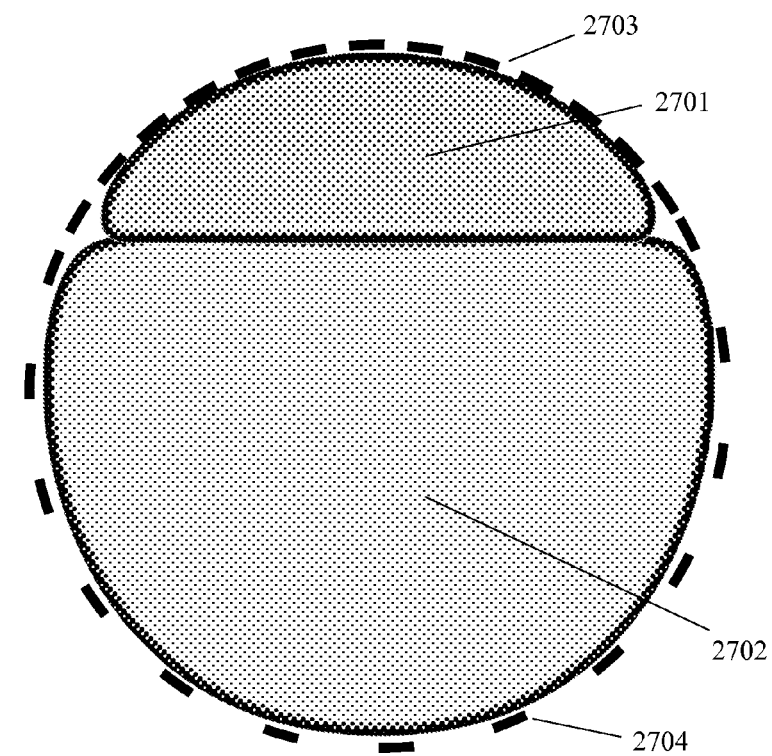

FIGS. 27-28 show lateral cross-sectional views of a tubular stent as it is non-uniformly expanded by differential inflation of two longitudinal expandable members in order to create non-uniform post-expansion wall porosity. FIG. 27 shows a lateral cross section of this tubular stent, with two inflatable members inside, before expansion. FIG. 28 shows this lateral cross section of this tubular stent after expansion. The circular dashed line in FIG. 27 represents a lateral cross-sectional view of the tubular stent mesh, including the upper cross-sectional portion of the mesh 2703 and the lower cross-sectional portion of the mesh 2704. FIG. 27 shows lateral cross-sections of two longitudinal inflatable members, 2701 and 2702, inside the tubular stent. In this example, these longitudinal inflatable members are balloons. In this example, the longitudinal axes of these inflatable members are parallel to the longitudinal axis of the stent.

FIG. 28 shows this same stent after differential inflation of balloon 2702 more than balloon 2701. In FIG. 28, differential inflation of these two balloons has caused non-uniform expansion of the stent which has, in turn, caused differential wall porosity. The upper portion of the stent cross section, 2703, has a lower post-expansion wall porosity than the lower portion of the stent cross section, 2704. In this example, the overall tubular shape of the stent is maintained despite differential wall porosity. FIGS. 27-28 may be viewed as lateral cross-sectional views of the same (or very similar) stent as the stent whose non-uniform expansion was shown, in longitudinal cross-section views, in FIGS. 23-24.

Figure 29:
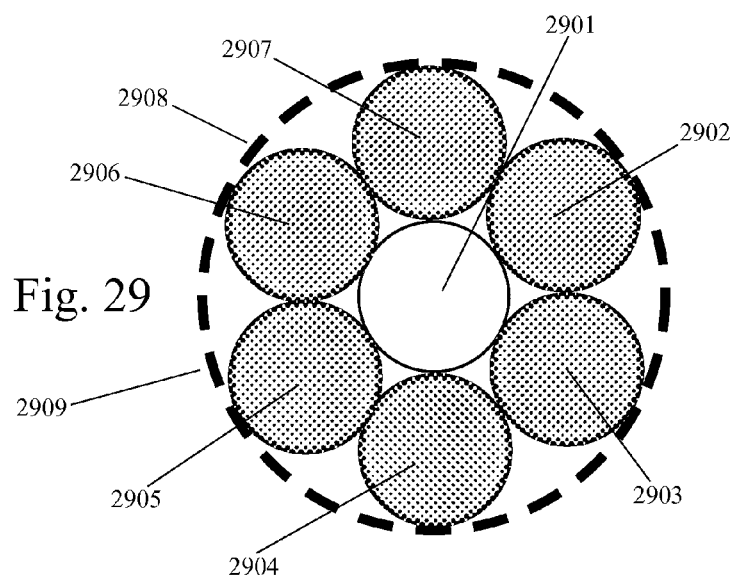
Figure 30:
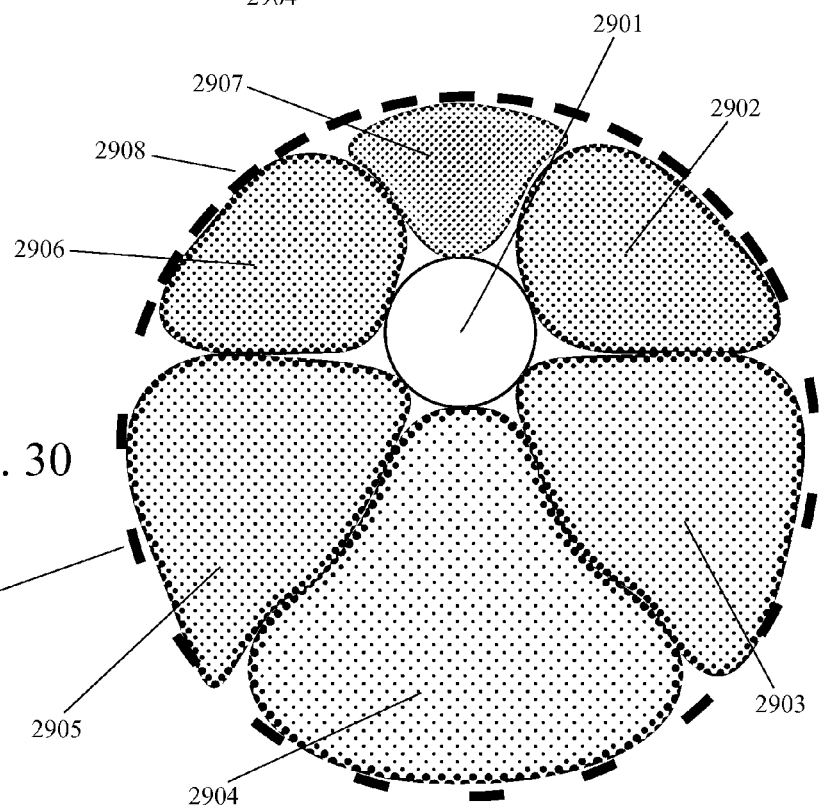

FIGS. 29-30 show another example of how this invention may be embodied using differential inflation of multiple inflatable members to create non-uniform stent expansion, which in turn creates differential post-expansion wall porosity. FIG. 29 shows a lateral cross-sectional view of a tubular expandable mesh, including upper mesh portion 2908 and lower mesh portion 2909. FIG. 29 also shows lateral cross-sections of six longitudinal inflatable members (2902, 2903, 2904, 2905, 2906, and 2907) that are arranged in a radially-symmetric and parallel manner inside this tubular mesh. In this example, there is also a non-inflatable flexible core,

2901, along the pre-expansion central longitudinal axis of the tubular mesh. In this example, the six inflatable members (2902-2907) surround this core (2901) in a radially-symmetric manner.

FIG. 30 shows this tubular mesh after it has been non-uniformly expanded by differential inflation of the six inflatable members. The inflatable members toward the bottom of the mesh cross-section (2903, 2904, and 2905) have been inflated more than inflatable members toward the top of the mesh cross-section (2902, 2906, and 2907). As a result of this differential inflation and non-uniform expansion, the upper portion of the stent, 2908, has lower post-expansion porosity than the lower portion of the stent, 2909.

In this example, there are six longitudinal, parallel, radially-symmetric inflatable members inside the stent which are differentially inflated to cause non-uniform expansion. In other examples, there may be more or less than six inflatable members. In other examples, the inflatable members may not be parallel. In other examples, the inflatable members may not be radially symmetric. In this example, the six members are separate and not attached to each other. In other examples, the inflatable members may either be attached to each other or may be separately-inflatable chambers within a single inflatable member.

In various examples, this invention may be embodied using other means of non-uniform expansion to determine differential wall porosity in situ. In various examples, a stent may be expanded by a means selected from the following group: self-expansion of non-shape-memory material; expansion of shape memory material; inflation of one or more inflatable members; and activation of Micro-Electro-Mechanical Systems (MEMS).

In an example, this invention may be embodied as a stent that is expanded using Micro-Electro-Mechanical Systems (MEMS). In an example, the locations on the stent wall of the one or more post-expansion cross-sectional perimeter differences in wall porosity or post-expansion longitudinal differences in wall porosity are selectively determined, after insertion of the stent, by the selective activation of one or more Micro-Electro-Mechanical Systems (MEMS) among a plurality of MEMS, wherein these MEMS selectively move different areas, respectively, of the stent wall.

In an example, this invention may be embodied as a stent that is expanded using shape-memory members. In an example, the locations on the stent wall of the one or more post-expansion cross-sectional perimeter differences in wall porosity or post-expansion longitudinal differences in wall porosity are selectively determined after insertion of the stent by the selection of, and application of energy to, one or more shape-memory members among a plurality of shape-memory members, wherein these shape-memory members selectively move different areas, respectively, of the stent wall.

In various examples, this invention may be embodied as a method of creating low-porosity wall areas in a stent comprising: (1) inserting the stent into a blood vessel; and (2) selectively determining one or more post-expansion low-porosity wall areas after insertion of the stent and before expansion of the stent using a means selected from the group consisting of: (a) detaching, removing, or stretching one or more expansion-resisting members among a plurality of expansion-resisting members, wherein these expansion-resisting members selectively restrict expansion of different areas of the stent wall, prior to expansion of the stent; (b) inflating one or more inflatable members among a plurality of inflatable members, or a plurality of chambers in a single inflatable member, wherein these inflatable members or chambers selectively expand different areas, respectively, of the stent wall; (c) activating one or more Micro-Electro-Mechanical Systems (MEMS) among a plurality of MEMS, wherein these MEMS selectively move different areas, respectively, of the stent wall; and (d) applying energy to, one or more shape-memory members among a plurality of shape-memory members, wherein these shape-memory members selectively move different areas, respectively, of the stent wall.

We claim:

1. A method of creating differences in porosity between portions of a cross-sectional perimeter of a stent wall comprising:
    inserting a stent into a blood vessel, wherein the stent has multiple cross-sectional perimeters including a selected cross-sectional perimeter;
    expanding a first portion of the selected cross-sectional perimeter of the stent by inflating a first inflatable member, wherein the first portion has a first porosity level before inflation of the first inflatable member and a second porosity level after inflation of the first inflatable member;
    expanding a second portion of the selected cross-sectional perimeter of the stent by inflating a second inflatable member, wherein the second portion has a third porosity level before inflation of the second inflatable member and a fourth porosity level after inflation of the second inflatable member, wherein the difference between the second porosity level and the fourth porosity level is greater than the difference between the first porosity level and the third porosity level, wherein the first inflatable member and the second inflatable member each have a lateral cross section that spans a portion of the interior of the selected cross-sectional perimeter of the stent, and wherein there is a non-inflatable core between the first inflatable member and the second inflatable member; and
    removing the first inflatable member, the second inflatable member, and the non-inflatable core from the stent.

* * * * *